United States Patent [19]

Reed et al.

[11] Patent Number: 5,419,966
[45] Date of Patent: May 30, 1995

[54] SOLID SUPPORT FOR SYNTHESIS OF 3'-TAILED OLIGONUCLEOTIDES

[75] Inventors: Michael W. Reed, Seattle; Rich B. Meyer, Jr.; Charles R. Petrie, both of Woodinville; John C. Tabone, Bothell, all of Wash.

[73] Assignee: MicroProbe Corporation, Bothell, Wash.

[21] Appl. No.: 90,408

[22] Filed: Jul. 12, 1993

Related U.S. Application Data

[62] Division of Ser. No. 714,142, Jun. 10, 1991, abandoned.

[51] Int. Cl.$^6$ .................. C07D 209/48; C07H 21/04; C07C 15/14
[52] U.S. Cl. .................. 428/406; 536/25.3; 548/473; 552/101
[58] Field of Search .................. 423/325; 536/25.3; 552/101; 548/478, 473; 428/406

[56] References Cited

PUBLICATIONS

T. Saison-Behmoaras, et al., "Short Modified Antisense Oligonucleotides Directed Against Ha-ras Point Mutation Induce Selective Cleavage of the mRNA and Inhibit T24 Cells Proliferation", the EMBO Journal vol. 10, No. 5, pp. 1111–1118, 1991.

Frank Seela, et al., "Oligodeoxyribonucleotides Containing 1,3-Propanediol As Nucleoside Substitute", IRL Press Limited, Oxford, England, Nucleic Acids Research, vol. 15, No. 7, 1987.

Robert L. Letsinger, et al., "Cholesteryl-conjugated Oligonucleotides: Synthesis, Properties, and Activity as Inhibitors of Republication of Human Immunodeficiency Virus in Cell Culture", Proc., Natl. Acad, Sci, USA, vol. 86, pp. 6553–6556, Sep. 1989, Biochemistry.

Ulysse Asseline, et al., "Nucleic Acid≧Binding Molecules with High Affinity and Base Sequence Specificity: Intercalating Agents Covalently Linked to Oligodeoxynucleotides", Proc. Natl. Acad. Sci, U.S.A., vol. 81, pp. 3297–3301, Jun. 1984, Biochemistry.

Paul S. Nelson, et al., "Bifunctional Oligonucleotide Probes Synthesized Using a Novel CPG Support Art Able to Detect Single Base Pair Mutations", Nucleic Acids Research, vol. 17, No. 18, 1989, pp. 7187–7194.

J. Synese, et al., Chem. Abst. 106: 213981q, p. 652, vol. 106, 1987.

Michael W. Reed, et al., "Acrinidine-and Cholesterol-Derivatized Solid Supports for Improved Synthesis of 3'-Modified Oligonucleotides", Bioconjugate Chemistry, No. 2, American Chemical Society, 1991, pp. 217–225.

(List continued on next page.)

Primary Examiner—Douglas W. Robinson
Assistant Examiner—Gary Kunz
Attorney, Agent, or Firm—Klein & Szekeres

[57] ABSTRACT

A solid support for oligonucleotide synthesis has the structure

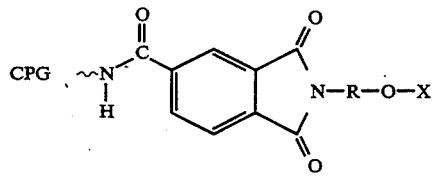

where CPG represents a controlled pore glass matrix, the wavy line represents a carbon chain covalently linking the NH group with the controlled pore glass matrix, X is 2,2'-dimethoxytrityl or H, and R is alkyl, aryl, arylalkyl, heteroalkyl, or heteroaryl. The dimethoxytrityl group is removed from the solid support by treatment with acid, and the oligonucleotide is built, step-by-step in a conventional synthesizer after attachment of the 3' end of the first oligonucleotide unit to the hydroxyl function connected to the R group.

5 Claims, 3 Drawing Sheets

PUBLICATIONS

R. T. Pon et al., "Derivatization of Controlled Pore Glass Beads for Slid Phase Oligonuleotide Synthesis", BioTechniques, 6(8): 768–775 (1988).

T. Atkinson et al., "Solid-PHase Synthesis of Oligodeoxyribonucleotides by the Phosphite-triester Method," Oligonucleotide Synthesis, A. Practical Approach, M. J. Gait, ed. IRL Press, pp. 35–81 (1984).

J. C. Francois et al., "Periodic Cleavage of Poly(dA) by Oligothymidylates Covalently Linked to the 1,10-Phenanthrioline–Copper Complex," Biochemistry 27: 2272–76 (1988).

G. B. Dreyer et al., "Sequence-Specific Cleavage of Single-Stranded DNA: Oligodeoxynucleotide-EDTA.FE(II)," Proc. Natl. Acad. Sci. U.S.A. 82: 968–72 (Feb. 1985).

C. F. Stanfield et al., "Synthesis of Protected Animo Alcohols: A Comparative Study," J. Org. Chem. 46: 4799–4800 (1981).

SOLID SUPPORT FOR SYNTHESIS OF 3'-TAILED OLIGONUCLEOTIDES

This is a Divisional of parent case Ser. No. 07/714,142 filed Jun. 10, 1991, now abandoned.

BACKGROUND OF THE INVENTION

This invention is directed to a method of synthesis of oligonucleotides having low molecular weight tail molecules joined to the 3'-terminus of the oligonucleotide via a linking molecule, to oligonucleotides having low molecular weight tail molecules joined to their 3'-terminus and to intermediates utilized for the synthesis of such oligonucleotides.

Oligonucleotides have various uses including acting as primers for polymerase chain reaction synthesis of DNA. Oligodeoxynucleotides (abbreviated as ODN) are conveniently synthesized on solid phase supports using phosphite-triester synthetic methods. A detailed review of such syntheses was published in Atkinson, T., Smith, M. (1984) in *Oligonucleotide Synthesis, A Practical Approach*, Gait, M. J. (ed.), IRL Press, pp. 35–81. This review gives detailed step by step conditions for the practical synthesis of oligonucleotides. Indeed, methods as outlined in this review are presently utilized in commercial oligonucleotide synthesizers available from various manufacturers.

Asseline et al., *Proc. Natl. Acad. Sci.* 81:3297–3301 (1984), describes the synthesis of certain oligonucleotides wherein an intercalating agent was covalently linked to the oligodeoxynucleotides. The intercalating agent utilized was 2-methoxy-6-chloro-9-aminoacridine. The acridine molecule was covalently linked to an oligodeoxynucleotide via a methylene chain of from 3 to 6 carbon atoms connecting the 3'-phosphate of the oligodeoxynucleotide to the 9-amino group of the acridine. The authors of this study found that the acridine modified oligonucleotides in the presence of a complementary sequence showed strong stabilization by the intercalating agent, i.e., the acridine. These authors measured certain thermodynamic parameters and showed via these parameters that the covalent attachment of the acridine ring strongly stabilized the binding of a synthetic oligonucleotide to its complementary sequence. The melting temperature, i.e., $T_m$, of an oligonucleotide having the intercalating agent attached thereto and its complementary strand was increased compared to the melting temperature of a similar oligonucleotide not bearing the intercalating agent thereon and its complementary strand. The authors concluded that the results clearly show that the presence of the intercalating agent strongly stabilized the complex formed between an oligonucleotide and its complementary strand.

In a similar study Letsinger et al., *Proc. Natl. Acad. Sci.* 86:6553–6556 (1989), prepared a family of oligonucleotides that had a cholesteryl group covalently joined at the 3'-terminal internucleoside phosphate linkage. Oligomers of various length were synthesized. Those bearing the cholesteryl moiety adjacent either the 3' terminus or both the 3' and the 5' terminus were compared to oligomers that were not so substituted. These compounds were tested as to their inhibitory action on HIV-1 replication. Anchoring of a single cholesteryl fragment adjacent to the 3' terminus of a 20-mer oligonucleotide significantly enhanced the antiviral activity of the oligonucleotide. Anchoring of the second cholesteryl fragment at the 5' terminus of the oligonucleotide detracted and led to a reduction of activity compared to the monocholesteryl derivatized oligomer.

The compounds of Letsinger et al. were prepared by first manually preparing a support bound dinucleoside hydrogen phosphonate derivative. A cholesteryl group was then tethered to the internucleoside phosphorus by oxidative phosphoramidation. The oligonucleotide was elongated from the original dinucleotide on a commercial DNA synthesizer using phosphoramidite chemistry.

Controlled pore glass beads for use in commercial oligonucleotide synthesis are available from CPG, Inc., Pierce Chemical Co. and Sigma Chemical Co. As is described in Atkinson and Smith, above, the controlled pore glass beads, hereinafter alternately referred to as CPG's, are derivatized by the manufacturers with a long chain alkylamine group, such that a free amino group is available at the end of the long chain alkylamine that in turn is attached to the CPG. Various amide linkages can be formed with the terminal amine of the long chain alkylamine on the CPG's for attachment of a growing oligonucleotide during synthesis of the same. An improvement of this synthesis was reported by Pon et al., *BioTechniques* 6(8):768 (1988). In this report Pon et al. precap a suspected contaminate side group on the long chain alkylamine CPG and introduce the use of DEC (a water soluble carbodiimide, i.e., 1-(3-dimethylaminopropyl)-3-ethylcarbodiimide or EDC) in place of the more commonly used (and toxic) linking agent DCC, i.e., dicyclohexylcarbodiimide.

Nelson et al., *Nuc. Acids Research* 17(18):7187–7194 (1989), recently described the synthesis of an oligonucleotide incorporating a 3'-terminal substituent thereon. To prepare a 3'-tailed oligonucleotide, Nelson et al. derivatized the secondary hydroxyl of N-Fmoc-O-DMT-3-amino-1,2-propanediol by treating with succinic anhydride in the presence of DMAP (dimethylaminopyridine), and then subsequently treated with p-nitrophenol in DCC. The activated derivative was then anchored to a long chain alkylamine CPG support. The dimethoxytrityl blocking group was removed from the primary alcohol of the propanediol and an oligonucleotide was synthesized stepwise from the primary hydroxyl group while supported on the CPG support. The synthetic oligonucleotide was deprotected and cleaved from the CPG support. However, the purity of this 3'-amine-modified oligonucleotide was not demonstrated. At this juncture in this synthesis, the 3'-terminal tail substituent has yet to be coupled to the oligonucleotide. The crude oligonucleotide was biotinylated with a "Biotin-XX-NHS" ester. After biotinylation, a second purification was necessary by both Sephadex and by HPLC. No yield data were given.

The above procedure of Nelson et al. gives an oligonucleotide with an amine functional group that may be derivatized (modified) with a "tailing reagent", then repurified. However, the derivation with the "tailing reagent" is effected only after the synthesis of the oligonucleotide is complete. By effecting the derivation on a completed oligonucleotide, precious oligonucleotide that has been systematically stepwise assembled, nucleotide by nucleotide, can be lost to incomplete reaction, side reactions and/or multiple purifications necessary after the derivation. Additionally, this synthesis did not take advantage of the above Pon et al. improvement.

BRIEF DESCRIPTION OF THE INVENTION

The usefulness of oligonucleotides can be enhanced by including small molecular weight groups at their 3' end as, for instance, the above referred to 3'-tailed cholesterol and 3'-tailed acridine oligonucleotides of Letsinger et al. and Asseline et al. The stability of 3'-tailed oligonucleotides in serum may also be enhanced. For instance, unmodified ODNs are rapidly degraded by 3'-exonucleases in serum-containing media. Certain chemical modifications of the 3'-terminal phosphodiester bond can block this degradation. Shaw et al., Nucl Acids Res. 19(4):747 (1991) reported that changing the last two internucleotidic phosphodiester bonds to phosphorothioates, phosphoroamidates, or inverted linkages significantly improved stability to nucleases. Other linkages that have been shown to improve nuclease stability are α-deoxynucleotide derivatives and methylphosphonate derivatives.

In one aspect of the present invention, it is a broad object to provide an improved method of synthesis of oligonucleotides having low molecular weight tail molecules joined to the 3' terminus of the oligonucleotide. It is a further object to provide a method of synthesis of oligonucleotides having a low molecular weight molecule joined to the oligomer via a linking molecule. It is an additional object of this invention to provide for oligonucleotides derivatized about their 3' terminus with a phosphate ester and a tail molecule joined to that phosphate ester. It is a further object to provide for a linking molecule and a support system suitable for the preparation of oligonucleotides thereon. Further, it is an object to provide for a linking molecule bearing an appropriate small molecular weight molecule onto which an oligonucleotide can be constructed.

A second aspect of the present invention discloses a linking molecule bearing a protected amine group onto which an oligonucleotide can be constructed. A third aspect of the claimed invention provides "tailing reagents" bearing an intercalating group that can be added to amine-modified oligonucleotides. A fourth aspect of the invention describes a linking molecule bearing a protected alkanol group onto which an oligonucleotide can be constructed.

These and other objects as will become evident from the remainder of this specification are achieved in a method of synthesis of an oligonucleotide having a low molecular weight tail molecule joined to its 3' terminus via a linking molecule. The method of the first aspect includes selecting as the linking molecule a molecule having three independent functional groups with the chemical reactivity of each of the three functional groups being independent and distinct from the reactivity of the other two of the functional groups. The first functional group of the linking molecule is reacted with a low molecular weight tail molecule to join the tail molecule to the linking molecule. The second functional group of the linking molecule is treated with succinic anhydride; the resulting carboxylic acid residue is reacted with a solid phase support to connect or anchor the linking molecule having the tail molecule joined thereto to the solid phase support.

Throughout this description, attachment of a hydroxyl-bearing linking moiety (for instance, "R-OH") to a solid support is accomplished via a succinate linkage, as described above. Thus, in the formula "support-O-R", the "support-O" designation includes such succinate linkage.

A first 3'- phosphoramidite nucleotide is then reacted with the third functional group of the linking molecule to attach the first nucleotide via its 3' terminus to the linking molecule. The attachment of the first nucleotide to the linking molecule joins the first nucleotide to the tail molecule via the linking molecule and connects or anchors the first nucleotide to the solid phase support also via the linking molecule. Further 3'-phosphoramidite nucleotides are subsequently reacted with the 5' end of a preceding nucleotide to form a synthetic oligonucleotide attached to the linking molecule at the oligonucleotide's 3' terminus. As with the first nucleotide, the attachment of the synthetic oligonucleotide via its 3' terminus to the linking molecule concurrently joins the oligonucleotide to the tail molecule and to the solid phase support. Thus the growing oligonucleotide is attached to the solid phase support during the reactions of the further nucleotides with the growing oligonucleotide. The oligonucleotide having the tail molecule joined to its 3' terminus via the linking molecule is then disconnected from the solid phase support by cleaving the connection between the second functional group of the linking molecule and the solid phase support. The oligonucleotide having the tail molecule joined to its 3' terminus via the linking molecule can then be isolated.

In a preferred embodiment of this first aspect of the invention, the functional groups on the linking molecule include a primary alcohol, a secondary alcohol and an amine. The tail molecule is reacted with the amine to join the tail molecule to the linking molecule, the solid phase support is reacted with the secondary alcohol to connect the linking molecule having the tail molecule joined thereto to the solid phase support and the first phosphoramidite nucleotide is reacted with the primary alcohol to attach that first nucleotide to the linking molecule.

Particularly preferred as the linking molecule is (2S,4R)-4-hydroxy-2-hydroxymethylpyrrolidine (also designated as 4-hydroxy-(2s-trans)-2-pyrrolidinemethanol or trans-4-hydroxy-L-prolinol).

The tail molecule can be selected as any one of a number of molecules of interest including reporter groups, intercalating groups, lipophilic groups and cleaving groups. Suitable as a lipophilic group would be cholesterol. Suitable as a reporter group would be biotin and fluorophores including acridine, fluorescein, rhodamine, Lissamine rhodamine B, Malachite Green, erythrosin, tetramethylrhodamine, eosin, pyrene, anthracene, 4-dimethylaminonaphthalene, 2-dimethylaminonaphthalene, 7-dimethylamino-4-methylcoumarin, 7-dimethylaminocoumarin, 7-hydroxy-4-methylcoumarin, 7-hydroxycoumarin, 7-methoxycoumarin, 7-acetoxycoumarin, 7-diethylamino-3-phenyl-4-methylcoumarin, isoluminol, benzophenone, dansyl, dabsyl, mansyl, sulforhodamine, 4-acetamido-4'-stilbene-2,2'-disulfonic acid disodium salt, and 4-benzamido-4'-stilbene-2,2'-disulfonic acid disodium salt. Suitable as an intercalating group would be acridine, ellipticine, methidium, ethidium, phenanthroline, 2-hydroxy-ethanethiolato-2,2',2''-terpyridine-platinum-(II) and quinoxaline and suitable as a cleaving group would be an EDTA ligand or porphyrin ligand for attaching Fe and a phenanthroline ligand for attaching Cu.

For reaction with the amine of the linking molecule, the tail molecule can be selected to include an inherent connecting group or an appendant connecting group can be attached to it via an appropriate chemical synthesis. If used, after attachment, the appendant connecting group, like an inherent connecting group, is used to link the tail molecule to the linking molecule. Whether or not an inherent or an appendant connecting group is utilized, the connecting group is such that it reacts with the linking molecule to attach the tail molecule to the linking molecule.

After attaching the tail molecule to the linking molecule via the first functional group but prior to joining the linking molecule to the solid state support, the third functional group of the linking molecule can be selectively blocked. The linking molecule bearing the blocked third functional group is then attached to the solid state support via the second functional group. The third functional group is then deblocked and the first phosphoramidite nucleotide is attached to the linking molecule via the deblocked third functional group.

The objects of the first aspect of the present invention are further achieved in a derivatized oligonucleotide having a 3'-terminal hydroxyl. A phosphate ester is located on that 3'-terminal hydroxyl and is of the structure:

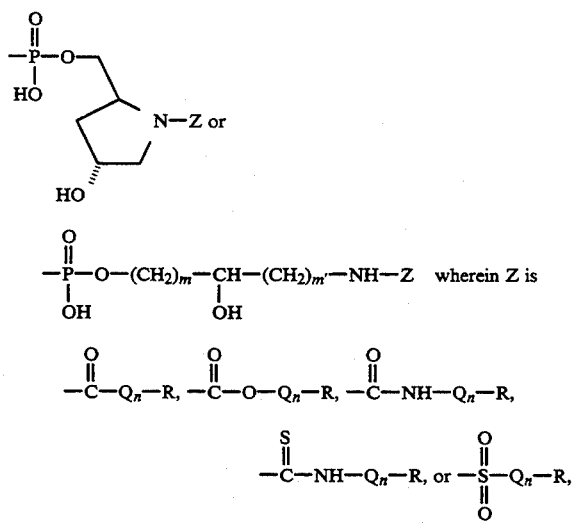

$$-\text{P}-\text{O}-(\text{CH}_2)_m-\text{CH}-(\text{CH}_2)_{m'}-\text{NH}-\text{Z} \quad \text{wherein Z is}$$
$$\quad\quad\quad\quad\quad\quad\quad |$$
$$\quad\quad\quad\quad\quad\quad\quad \text{OH}$$

with OH on the P also.

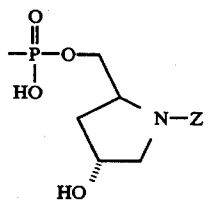

m and m' independently are positive integers less than 11, n is 0 or 1, Q is a connecting group and R is selected from the group consisting of reporter groups, intercalating groups, lipophilic groups and cleaving groups.

Of this group, particularly preferred are compounds of the structure:

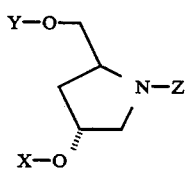

Particularly preferred 3'-tailed oligonucleotides would include an oligonucleotide having either cholesterol or acridine joined via a linking molecule to the oligomer's 3' tail. The cholesterol moiety is bonded to the linking molecule utilizing a carbamate linkage and the acridine moiety, preferably 9-ethylacridine or another 9-alkylacridine, is joined to the oligonucleotide utilizing an amide linkage (in effect an alkylamine linkage if the ethyl group of the 9-ethylacridine is considered). Other tail groups can be joined to the linking molecule via urea, thiourea or sulfonamide linkages.

In attaching the tail molecule to the linking molecule, the connecting group Q can preferably be selected from the group consisting of alkyl, alkoxy, alkoxyalkyl, alkenyl, cycloalkyl, aryl, aryloxy, aralkyl, heterocyclic, heteroaryl, substituted aryl and substituted aralkyl.

Further objects of the first aspect of the invention are achieved in a compound and support for oligonucleotide synthesis comprising: a compound of the structure:

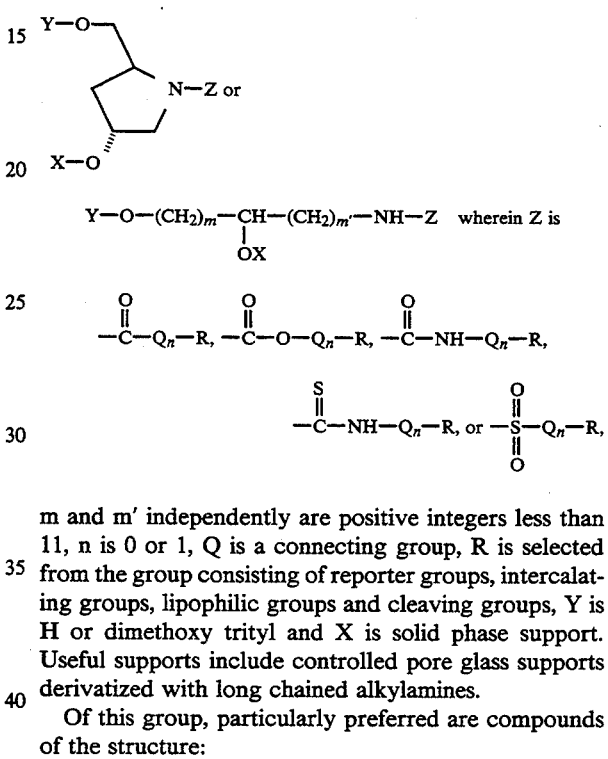

m and m' independently are positive integers less than 11, n is 0 or 1, Q is a connecting group, R is selected from the group consisting of reporter groups, intercalating groups, lipophilic groups and cleaving groups, Y is H or dimethoxy trityl and X is solid phase support. Useful supports include controlled pore glass supports derivatized with long chained alkylamines.

Of this group, particularly preferred are compounds of the structure:

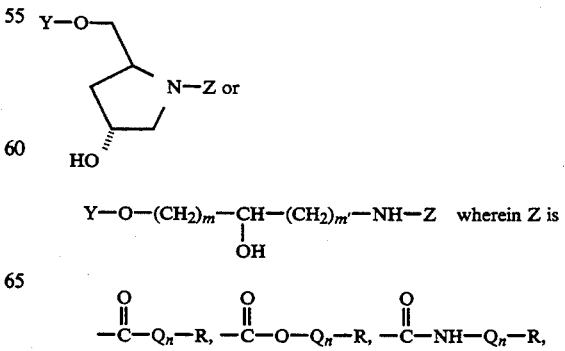

The objects of the first aspect of the present invention are further achieved in a compound of the structure:

-continued

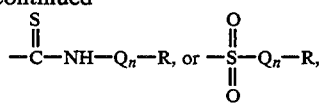

m and m' independently are positive integers less than 11, n is 0 or 1, Q is a connecting group, R is selected from the group consisting of reporter groups, intercalating groups, lipophilic groups and cleaving groups and Y is H or dimethoxy trityl.

Of this group, particularly preferred are compounds of the structure:

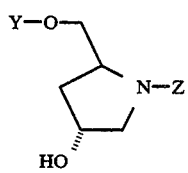

In each of the above structures, m and m' are positive integers less than 11, that is m and m' independently are 1, 2, 3, 4, 5, 6, 7, 8, 9 or 10. Particularly preferred are compounds wherein m and m' are 6 or less that is m and m' independently are 1, 2, 3, 4, 5 or 6.

Another aspect of the claimed invention provides improved compounds and methods for synthesis of tetrafluorophenyl (TFP) esters of carboxylic acids in general. An exemplary method provides improved synthesis of an activated ester derivative of an acridinyl carboxylic acid. Such activated ester derivative may be advantageously used: (1) for making acridine-CPG, which in turn may be used to make 3'-tailed oligonucleotides; (2) for post-synthetic modification of 3'-amine-tailed oligonucleotides; and (3) for modification of internally amine-modified oligonucleotides.

Further aspects of the present invention disclose aminohexyl-modified solid supports and hexanol-modified solid supports that may be advantageously used for synthesis of 3'-tailed oligonucleotides.

DETAILED DESCRIPTION OF THE INVENTION

Figure 1:
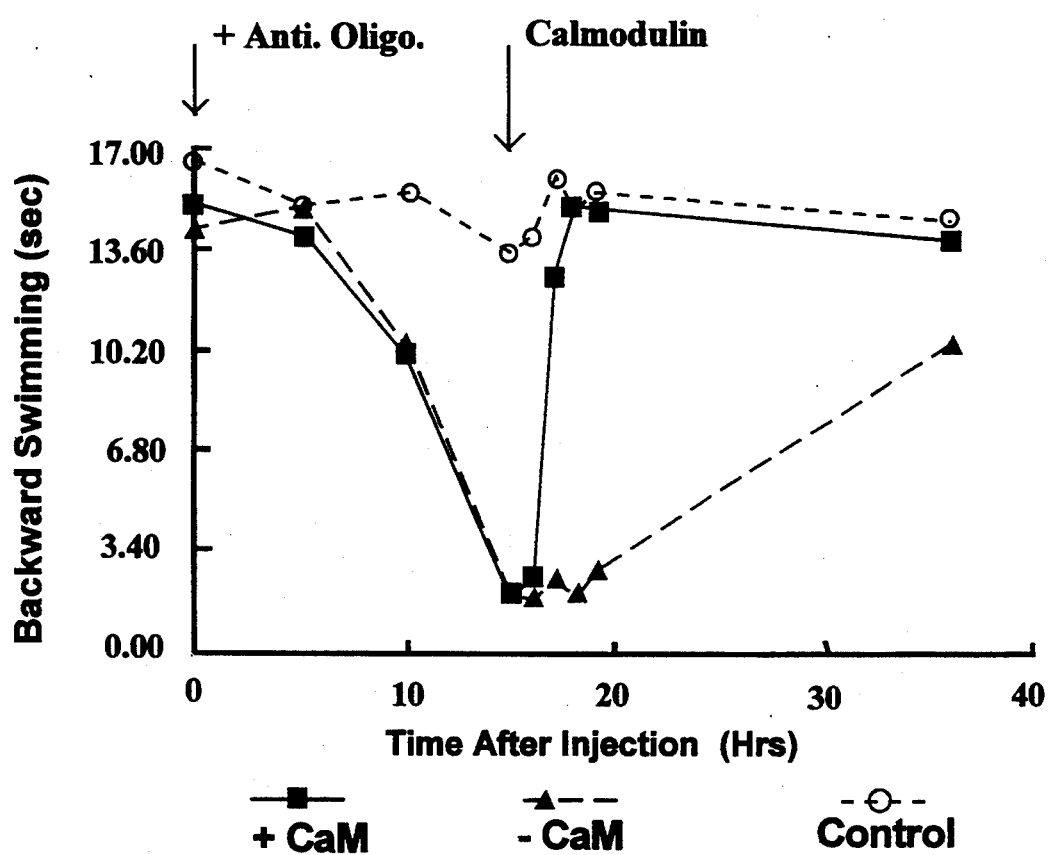
FIG. 1 shows the time course of swimming behavior of Paramecium after microinjection of antisense ODN 39.

A.1. Modified Solid Supports Having a 3'-Tail for Direct Synthesis of 3'-Tailed Oligonucleotides (Method A)

We have found that an oligonucleotide can be synthesized having a low molecular tail molecule joined to the 3' terminus of the oligonucleotide by use of a linking molecule. The linking molecule is selected to have three chemically distinct functional groups on it. When such a linking molecule is utilized, a low molecular weight tail molecule is first joined to the linking molecule. The linking molecule with its low molecular weight tail molecule is then joined or anchored to a solid phase support. The oligonucleotide is then synthesized. During its synthesis, the oligonucleotide is anchored on the linking molecule which in turn is anchored to the solid state support system. The oligonucleotide is synthesized using standard phosphoramidite chemistry, either manually or on a DNA synthesizer. When the synthesis of the oligonucleotide is completed, the linking molecule having the synthesized oligonucleotide and a low molecular weight tail molecule joined to it, is cleaved from the solid state support. This frees the oligonucleotide from the support system. The oligonucleotide now has the small molecular weight tail molecule joined to its 3' terminus via the linking molecule.

Using the above preparative steps oligonucleotides having low molecular weight tail molecules joined to their 3' terminus need only be subjected to a single purification step. Thus, compared to the prior art, oligonucleotides having molecules of interest joined to their 3' terminus are prepared in a facile and expeditious manner.

The linking molecule having an appropriate low molecular weight molecule of interest attached to it can be synthesized independent of the oligonucleotide synthesis. Once a linking molecule having a tail molecule of interest linked thereto is prepared by reacting the tail molecule with the first functional group of the linking molecule, the combination of the linking molecule and the tail molecule can be considered as a reagent suitable for use in a DNA synthesizer for preparation of numerous different oligonucleotides each of which have the low molecular weight molecule attached to their 3' terminus. This allows for large scale synthesis and storage, if desired, of the linking molecule-tail molecule combination. Additionally other combinations of the linking molecule with various other tail molecules also can be prepared in the same manner. These can then be used by non-organic chemical personnel for oligonucleotides synthesis using DNA synthesizers. Thus personnel not skilled in synthetic organic chemical disciplines can easily use aliquots of the linking molecule-tail molecule combinations as a first reagent in such automatic DNA synthesizers for synthesis of oligonucleotides having selected low molecular weight tail molecules joined to their 3' terminus.

Further, multiple oligonucleotides that may have a common sequence for a number of nucleotides and then a divergent sequence for the remainder of the oligonucleotides but all of which have the same 3'-tail molecule of interest attached via the linking molecule, can be prepared by simply subdividing into aliquots the solid state support having a partially formed "common" oligonucleotide and its attaching linking molecule and tail molecule of interest. The synthesis of the divergent segments of the oligonucleotides is then completing by loading an individual aliquot of the solid state support having the common segment of the oligonucleotide on the DNA synthesizer and completing the desired sequence of nucleotides.

The compound (2s,4R)-4-hydroxy-2-hydroxymethyl-pyrrolidine, compound 2 of Scheme I, (also identifiable as 4-hydroxy-(2s-trans)-2-pyrrolidinemethanol or trans-4-hydroxy-L-pyrolinol) serves as a particularly useful linking molecule for attaching molecules of interest to the 3' terminus of an oligonucleotide. This compound is readily prepared from commercially available N-CBZ-L-hydroxyproline (Sigma Chemical Company). Reduction of the N-CBZ-L-hydroxyproline utilizing a procedure similar to that described by Stanfield et al., *J. Org. Chem.* 46:4799 (1981) is readily accomplished using a borane-THF complex (Aldrich Chemical Co.). This reduction proceeds with retention of the optical purity to give compound 1. The CBZ protecting group in compound 1 is easily removed utilizing a palladium on charcoal reduction under a balloon of hydrogen. This reaction proceeds smoothly giving a quantitative yield of compound 2.

Compound 2 includes a primary hydroxyl group that is utilized as the foundation on which an oligonucleotide is synthesized. Further compound 2 includes a secondary alcohol group that is utilized for attachment to a solid state support and a secondary amine that is utilized for attaching a tail molecule of interest. After synthesis of the oligonucleotide is completed, the tail molecule of interest remains attached to the oligonucleotide via the linking molecule. After cleavage from the solid state support of the completed oligonucleotide including the molecule of interest joined thereto via the linking molecule, the secondary hydroxyl group of the linking molecule is essentially held rigid in space and is removed from the vicinity of the phosphate linkage that attaches the linking molecule to the first nucleoside. This results in increased stability of the bond between the linking molecule and the oligonucleotide's 3' terminal phosphate group.

Further, since compound 2 is a single optical isomer and is not a mixture of stereoisomers, the bond between the 3' terminus of the oligonucleotide and this linking molecule also yields a single isomer and not a mixture of stereoisomers that might affect the physical properties. This may be particularly importance when attaching intercalating groups or other reactive groups to the 3' terminus end of an oligonucleotide because of a potential requirement for precise geometry for optimum binding of the intercalating agent with the double stranded complex of the oligonucleotide and its complementary DNA segment.

Other linking molecules are compounds of the structure:

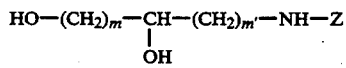

where m and m' are positive integers from 1 to 10, inclusive. These linking molecules also have an amino, a primary hydroxyl and a secondary hydroxyl functional group included in their structure. Two particularly useful linking molecules of this class are 3-amino-1,2-propanediol and 4-amino-1,3-butanediol (13) (see Scheme III).

Attachment of the tail compound of interest to the linking molecule is done completely independent of any oligonucleotide synthesis as described above. A low molecular weight tail molecule of interest is attached to the linking molecule utilizing organic chemistry techniques and reactions. The secondary amino group of linking molecule is utilized to link the low molecular weight tail molecule of interest to the linking molecule, e.g., compound 2, via any one of a number of suitable connections or linkage, as for instance an amide linkage, a carbamate linkage, an urea linkage, a thiourea linkage, or a sulfonamide linkage. Given this disclosure other suitable reactions between the secondary amine of linking molecule, e.g., compound 2, and appropriate connecting or linking groups on compounds of interest also will be suggested to the art skilled.

For the purposes of clarity of this specification and the claims attached hereto, to avoid confusion between the above referenced "linking molecule" and any further "linking group" that might be used to attach a tail molecule to this linking molecule, the terminology "connecting group" is utilized to indicated these connecting or linking groups. Irrespective of the name given to these groups, they link, connect or bond a tail molecule to the linking molecule.

After the molecule of interest, which eventually will be at the 3' tail of the oligonucleotide, is connected to the linking molecule, the primary hydroxyl group on the linking molecule is appropriately protected, as for instance with a dimethoxytrityl group. This is conveniently accomplished utilizing dimethoxytritylchloride (DMTrCl) in pyridine in the presence of 4-dimethylaminopyridine (DMAP). This selectively protects the primary alcohol group of the linking molecule. The secondary alcohol of the linking molecule is then converted to a succinate ester utilizing succinic anhydride. The succinic ester of the linking molecule bearing the low molecular weight compound of interest thereon can be coupled to a controlled pore glass support utilizing either the older p-nitrophenol-DCC method of Atkinson et al., above, or preferably using the facilitated DEC method of Pon et al., above. Insofar as DEC is less toxic than DCC, is water soluble and eliminates the necessity of treating the succinate ester with p-nitrophenol, it is the presently preferred method.

The dimethoxytrityl protected linking molecule bearing a low molecular weight compound of interest attached thereto is then coupled or anchored to a controlled pore glass support having a long chain alkylamine group attached thereto in the normal manner. Controlled pore glass supports derivatized with long chain alkylamines are available from Pierce Chemical or from Sigma Chemical. These are preactivated utilizing the procedure of Pon et al., above, with dichloroacetic acid and then reacted in pyridine utilizing DEC as the coupling reagent with the dimethoxytrityl protected linking molecule having the molecule of interest attached thereto. After attachment of the linking molecule to the solid state support, excess long chain alkylamino groups on the support are capped by acetylating the same with acetic anhydride.

The dimethoxytrityl group is removed from the primary alcohol of the linking molecule by treating with 3% dichloroacetic acid in dichloromethane. The resulting controlled pore glass support, having the low molecular weight tail molecule attached thereto via the linking molecule (and with the primary hydroxyl group of the linking molecule now deblocked), is now ready for synthesis of the oligonucleotide thereon. It is recognized that the solid state support loaded with the linking molecule and molecule of interest can also be prepared in bulk and then subdivided for the synthesis of multiple oligonucleotides or even stored for later use. In any event oligonucleotide synthesis is initiated from the primary hydroxyl group of the linking molecule using phosphoramidite chemistry on a DNA synthesizer, as for instance a Milligen DNA synthesizer, in a normal manner.

Once synthesis of the oligonucleotide is complete, the oligonucleotide is deprotected in the standard manner for oligonucleotides synthesized on automated DNA synthesizers. The oligonucleotide with the low molecular tail molecule joined to its 3' terminus via the linking molecule is then cleaved from the solid state support also in the normal manner for automated DNA synthesis utilizing concentrated ammonia at room temperature in the normal manner.

Only a single purification step is necessary to purify the oligonucleotide having the low molecular weight tail molecule joined to its 3' terminus via the linking molecule. This can conveniently be done utilizing reverse phase HPLC chromatography.

The low molecular weight tail molecule to be joined to the 3' terminus of the oligonucleotide can be any one of a number of molecules of biological interest. Included in this group would be reporter groups, intercalating groups, lipophilic groups and cleaving groups. Particularly preferred at this time for the lipophilic group is cholesterol. Particularly preferred at this time for reporter group are biotin and the fluorophores including acridine, fluorescein, rhodamine, Lissamine rhodamine B, Malachite Green, erythrosin, tetramethylrhodamine, eosin, pyrene, anthracene, 4-dimethylaminonaphthalene, 2-dimethylaminonaphthalene, 7-dimethyl-amino-4-methylcoumarin, 7-dimethylaminocoumarin, 7-hydroxy-4-methylcoumarin, 7-hydroxycoumarin, 7-methoxycoumarin, 7-acetoxycoumarin, 7-diethylamino-3-phenyl-4-methylcoumarin, isoluminol, benzophenone, dansyl, dabsyl, mansyl, sulfo rhodamine, 4-acetamido-4'-stilbene-2,2'-disulfonic acid disodium salt, 4-benzamido-4'-stilbene-2,2'-disulfonic acid disodium salt. Particularly preferred at this time for the intercalating group are acridine, ellipticine, methidium, ethidium, phenanthroline, 2-hydroxyethanethiolato-2,2',2''-terpyridine-platinum(II) and quinoxaline. Particularly preferred at this time for the cleaving group would be an EDTA ligand or porphyrin ligand for attaching iron and a phenanthroline ligand for attaching copper.

For those tail molecules that do not contain an inherent connecting group for attaching the tail molecule to the amino group of the linking molecule, the tail molecule is reacted with an appropriate reagent to attach an appendant connecting group thereon that is capable of reacting with the amine substituent of the linking molecule. Thus, irrespective of whether or not the tail molecule has an inherent connecting group that is capable of reacting with the amine of the linking molecule, or whether an appendant connecting group must be attached thereto for reacting with the amino group of the linking molecule, the tail molecule is reacted with the amino group of the linking molecule to attach the tail molecule to the linking molecule.

For attaching a tail molecule R via linking molecules

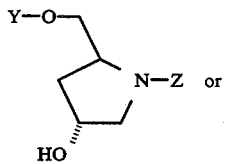

or

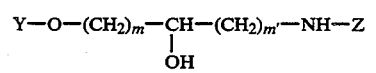

of the invention, Z is selected from one of the structures:

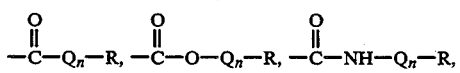

-continued

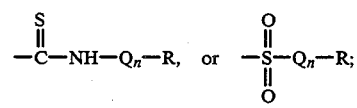

m and m' independently are selected to be positive integers less than 11, n is selected as 0 or 1, and Q is a connecting group. The tail molecule R is selected from the group consisting of reporter groups, intercalating groups, lipophilic groups and cleaving groups and Y is H or dimethoxytrityl.

As for instance, cholesterol chloroformate is reacted with the linking molecule to attach the cholesterol group to the linking molecule via a carbamate connecting group. In a further example, 9-acridinepropionic acid is reacted with the linking molecule yielding 9-ethylacridine attached linking molecule via an amide linkage (see Scheme II).

If the above referenced cholesterol chloroformate is used as the precursor of the tail molecule, n is 0 thus Q is absent and Z therefore is:

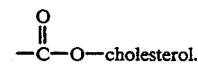

If the above referenced 9-acridinepropionic acid is used as the precursor of the tail molecule, n is 1 thus Q is present and is an alkyl moiety, i.e., ethyl (Scheme II). In this instance Z is:

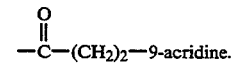

When n is 1 and Q is present, suitable for use as the connecting group Q are alkyl, alkoxy, alkoxyalkyl, alkenyl, cycloalkyl, aryl, aryloxy, aralkyl, heterocyclic, heteroaryl, substituted aryl and substituted aralkyl groups.

Useful as precursor molecules for preparations of compounds the above formula wherein Z is a carbamate of the structure:

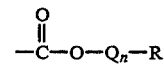

are chloroformates. Useful as precursor molecules for preparation of compounds of the above formula wherein Z is a urea of the structure:

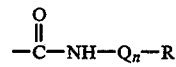

are isocyanates. Useful as precursor molecules for preparation of compounds of the above formula wherein Z is a thiourea of the structure:

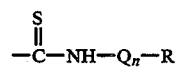

are isothiocyanates. Useful as precursor molecules for preparation of compounds of the above formula wherein Z is a sulfonamide of the structure:

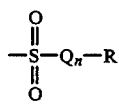

are sulfonyl halides.

Various sulfonyl halide precursors tail molecules are available from Molecular Probes, Inc., Eugene, Ore. Such sulfonyl halides are aromatic sulfonyl halides wherein the sulfonyl halide moiety is present as an inherent connecting moiety on one of the rings of a tail molecule of interest, as for instance a rhodamine, a naphthalene, a pyrene, or an anthracene ring. In such instance in the above formula n is 0 and the connecting group Q is therefore absent. Generally the halide ion is chlorine or fluorine however bromine and iodine might also be useful.

Useful sulfonyl halides include sulforhodamine, sold by Molecular Probes, Inc. under the tradename "Texas Red." Further would be Lissamine rhodamine B sulfonyl chloride, Lissamine rhodamine B sulfonyl fluoride, 5-dimethylaminonaphthalene-1-sulfonyl chloride (dansyl chloride), 2-dimethylaminonaphthalene-5-sulfonyl chloride, 2-dimethylaminonaphthalene-6-sulfonyl chloride, 6-(N-methylanilino)- naphthalene-2-sulfonyl chloride (mansyl chloride), 1-pyrenesulfonyl chloride, 2-anthracenesulfonyl chloride, 5-dimethylaminonaphthalene-1-sulfonyl fluoride (dansyl fluoride), and 4-dimethylaminoazobenzene-4'-sulfonyl chloride (dabsyl chloride).

Various isothiocyanates precursor tail molecules are useful for preparing thiourea linkages between the tail molecule and the linking molecule. As with the above sulfonyl halides, generally the isothiocyanates is present as an inherent connecting moiety on an aromatic ring of the tail molecule, and as such, in the above formula, n is also 0 and therefore Q would be absent. Such isothiocyanates are also available from Molecular Probes, Inc.

Suitable isothiocyanates for reacting with the linking molecule include fluorescein-5-isothiocyanate, fluorescein-6- isothiocyanate, tetramethylrhodamine-5-(and-6)-isothiocyanate, Rhodamine X isothiocyanate, Malachite Green isothiocyanate, eosin-5-isothiocyanate, erythrosin-5-isothiocyanate, 7-diethylamino-3-(4'-isothiocyanatophenyl)-4-methylcoumarin, p-(5-dimethylaminonaphthalene-1-sulfonyl)-aminophenylisothiocyanate, N-(4-(6-dimethylamino-2-benzofuranyl)-phenylisothiocyanate hydrochloride, 1-pyreneisothiocyanate, 2-anthraceneisothiocyanate, 4-dimethylaminonaphthyl-1-isothiocyanate, 9-acridine isothiocyanate, 4-isoluminol isothiocyanate, 4-dimethylaminophenylazophenyl-4'-isothiocyanate, benzophenone- 4-isothiocyanate, 4,4'-diisothiocyanatostilbene-2,2'-disulfonic acid disodium salt, 4,4'-diisothiocyanatodihydrostilbene-2,2'-disulfonic acid disodium salt, 4-acetamido-4'-isothiocyanatostilbene-2,2'-disulfonic acid disodium salt, and 4-benzamido-4'-isothiocyanatostilbene-2,2'-disulfonic acid disodium salt.

Other useful precursors molecules for the tail molecule including examples wherein n is i and thus a connecting group Q is present include tetrafluorophenyl (TFP) esters, 5-(and 6-)carboxyfluorescein diacetate succinimidyl ester, 7-dimethylaminocoumarin-4-acetic acid, 7-amino-4-methylcoumarin-3-acetic acid, 7-diethylaminocoumarin-3-carboxylic acid, 7-hydroxycoumarin-4-acetic acid, 7-hydroxy-4-methylcoumarin-3-acetic acid, 7-hydroxycoumarin-3-carboxylic acid, 7-methoxycoumarin-3-carboxylic acid, 7-carboxymethoxy-4-methylcoumarin, 7-acetoxycoumarin-3-carboxylic acid, acridone-2-acetic acid, acridone-10-acetic acid, 9-anthracenepropionic acid, 1-pyrenebutanoic acid (pyrenebutyric acid) and N-(5-dimethylaminonaphthalene-1-sulfonyl)glycine (dansyl glycine).

EDTA.Fe(II) has been used as a cleaving group in conjunction with an oligonucleotide. The EDTA molecule was attached to the base of a uridine nucleoside. A carboxyl terminated chain was extended from the uracil moiety and the EDTA attached to it. While this approach yields a nucleoside having EDTA attached to it, any oligonucleotide that incorporated such a nucleoside might suffer from the EDTA molecule interfering with initial base pairing between the oligomer and its complementary DNA stand, since the EDTA is on the base. By use of the linking molecule of this invention, an EDTA moiety can be extended from the linking molecule, away from the nucleotide's base and thus in a more non-interfering position for initial base pairing with a complementary stand of DNA.

Reaction of the linking molecule with an alkyl isocyanate, as for instance ethyl isocyanatoacetate, followed by treatment with ethylenediamine and EDTA-triethylester-N-hydroxysuccinimide ester, would serve to attach the EDTA moiety to the linking molecule via amide linkages. In this instance, an appendant connecting group is utilized to form the attaching bonds of the EDTA cleaving group with the linking molecule. Cleavage reaction conditions are initiated in aqueous solution by adding Fe(II) and an appropriate oxidant, such as dithiothreitol, in a manner as is set forth in Dreyer et al., *Proc. Natl. Acad. Sci.* 82:968-972 (1985).

In attaching a further cleaving group, phenanthroline-Cu(I) complex, 1,10-phenanthroline can be aminated at the 5 or 6 position. The amine can then be succinylated. The resulting terminal carboxylate would then be activated, as for instance by converting to an N-hydroxysuccinimide ester, for reaction with the amine of the linking molecule or with a further appendant connecting group that in turn is attached to the linking molecule. Cleavage with this reagent is initiated by the addition of cupric sulfate and mercaptopropionic acid in a manner similar to Francois et al., *Biochemistry* 27:2272-2276 (1988).

In a like manner, the secondary amino substituent of ellipticine might be directly succinylated with succinic anhydride in pyridine and then activated to the N-hydroxy succinimide ester (an NHS ester) with DCC in THF for attachment to the linking molecule. Quinoxaline requires amination of its ring, in a manner as per phenanthroline, prior to succinylation and activation.

Biotin having a long chain spacer is commercially available as a succinimidyl ester, also from Molecular Probes, Inc. This product, 6-(6-(biotinoylamino)hexanoylamino)hexanoic acid succinimidyl ester, is also referenced as biotin-XX-succinimidyl ester. In a manner equivalent to the above phenanthroline succinimidyl ester, it is reacted with the amino group of the linking molecule to join the biotin tail to the linking molecule. In a manner similar to Dervan et al., *J. Am. Chem. Soc.* 100:1968 (1978), p-carboxymethidium can be prepared for coupling to the linking molecule via its carboxylate group. In a like manner, ethidium might also be prepared.

A.2. Synthesis of Acridine TFP Esters and Improved Preparation of Acridine CPG The 9-acridinylalkanoic acids bind strongly to DNA (S. Takenaka et al., *Anal. Sci.* 4:481 (1988)), and can be prepared with a variety of different chain lengths. Acridine-modified ODNs have strict geometric requirements for efficient intercalation of the acridine molecule between the base pairs of a DNA duplex, but these geometric requirements are difficult to predict. Thus, it is preferred to have linking chain lengths that can be easily modified. In addition, a variety of linker arm lengths can be evaluated with respect to binding strength. The strength of binding of an oligonucleotide (ODN) to its complementary nucleic acid strand is readily determined through thermal denaturation ($T_m$) studies.

The 9-acridinylalkanoic acids may be prepared with a variety of alkyl chain lengths by heating the corresponding aliphatic diacid with diphenylamine and zinc chloride, using a modification of the method of H. Jensen and L. Howland, *J. Am. Chem. Soc.* 48:1926 (1989). For example, 45 gm (16% yield) of 5-(9-acridinyl)pentanoic acid were obtained from the condensation reaction with adipic acid. Two alkyl chain lengths used for preparation of acridine-CPG were selected to approximate the length previously reported to give optimal $T_m$ for other 3'-acridine tailed ODNs (U. Asseline et al., *Proc. Natl. Acad. Sci. USA* 81:3297 (1984)).

One embodiment of this aspect of the present invention provides an improved method for synthesis of acridine-CPG. This improved method uses an activated ester derivative of an acridinyl carboxylic acid as a precursor molecule. A variety of activated esters of acridinyl carboxylic acids were evaluated as potential precursors to acridine-CPG (10, 23). N-hydroxysuccinimide (NHS) esters and p-nitrophenyl esters were prepared by "activating" a carboxylic acid with dicyclohexylcarbodiimide (DCC), and then reacting with N-hydroxysuccinimide or p-nitrophenol. However, these condensation reactions are difficult to perform because the starting carboxylic acid and the dicyclohexylurea (DCU) side product are both insoluble in organic solvents commonly used for DCC activation. Further, these reactions did not go to completion, and the desired esters could not be easily purified by column chromatography on silica gel due to their instability. In contrast, TFP (tetrafluorophenyl) esters are suitably reactive with the nucleophilic amino group in trans-4-hydroxy-L-prolinol 2, yet stable enough to allow purification by flash chromatography.

An exemplary method for "activating" carboxylic acids to TFP esters is described. TFP ester 19 or 20 is prepared by first "activating" the carboxylic acid with 2-fluoro-methylpyridinium tosylate (FMPT), thereby forming an unstable intermediate, and then reacting this unstable intermediate with 2,3,5,6-tetrafluorophenol to provide the stable product, as shown in Scheme IV, Method a. No insoluble DCU is generated by this reaction, and the insoluble acridinyl carboxylic acid becomes soluble as the reaction proceeds. The resulting homogeneous mixture is stripped of solvent and purified by flash chromatography. FMPT is a particularly preferred activator for carboxylic acids that are not appreciably soluble in polar, aprotic organic solvents (such as ether, THF, DMF and acetonitrile).

The present invention also describes an improved reagent for preparation of TFP esters. Briefly, 2,3,5,6-tetrafluorophenol is treated with trifluoroacetic anhydride to provide TFP trifluoroacetate 18. This improved reagent 18 reacts with carboxylic acids in the presence of triethylamine to yield TFP esters, as shown in Scheme IV, Method b. For instance, 9-acridinylpropanoic acid may be treated with TFP trifluoroacetate 18 and triethylamine in methylene chloride to produce the desired acridinyl TFP ester 19.

Further, other carboxylic acids are suitable for reaction with TFP trifluoroacetate 18. Exemplary carboxylic acids in this regard include N-CBZ-L-phenylalanylglycine, protoporphyrin IX, 3-amino-9-ethylcarbazole succinamide and the like. Advantages of the disclosed reagent 18 and its method of use include: (1) TFP trifluoroacetate is readily prepared from inexpensive starting materials; (2) expensive condensing reagents are not required for production of TFP esters using this method of synthesis; and (3) improved purification of TFP ester product, since trifluoroacetate is the only by-product of the described reaction.

In a particularly preferred method (Example XXVIII; Method 2), acridine-CPG supports (10 and 23) are prepared from trans-4-hydroxy-n-prolinol 2 and the appropriate acridinyl-propionic or -pentanoic acid TFP ester (19 or 20), as shown in Scheme V. Purified TFP ester 19 or 20 is reacted with aminodiol 2 to give quantitative yield of the key intermediate amide product 7 or 21. This method (Method 2) provides more reproducible results than preparation of the diol amide 7 directly from acridine carboxylic acid via the intermediate N-methylpyridinium ester (Example XI; Method 1) (see Scheme II). The primary hydroxyl group in 7 or 21 is selectively protected as the DMTr ether using standard conditions and good yields of 8 or 22 are provided. The remaining secondary hydroxyl group is succinylated and the resulting carboxylic acids are immobilized on a long chain alkyl amine-controlled pore glass support (LCAA-CPG) to produce the desired Acr-CPG (10 or 23). The DMTr loading for these CPGs is 18.5 μmol/g and 20.6 μmol/g, respectively.

B. Post-Synthetic Modification of 3'-Amine-Modified ODNs Using Acridine TFP Esters (Method B)

3'-Tailed oligonucleotides may be directly synthesized from a solid support having a 3'-tail covalently attached thereto (Method A, as described in Sections A.1. and A.2). Alternatively, 3'-tailed ODNs may be synthesized using a specially prepared solid support that incorporates a protected nucleophilic amino group or thiol group. A conjugate group is then introduced into such 3'-tailed ODNs by post-synthetic treatment of the deprotected ODN with a suitable electrophile. In this aspect of the claimed invention, post-synthetic modification according to Method B is advantageously used to introduce sensitive 3'-tail molecules that cannot survive the synthesis conditions required for Method A. A further advantage of Method B relates to the large number of electrophilic conjugate groups that may be available on corresponding starting materials. Moreover, Method B is advantageously used for preparation of small quantities of modified ODNs.

The two methods for preparing 3'-tailed ODNs disclosed herein (Method A and Method B) were compared by examining the reaction of acridine TFP esters 19 and 20 with 3'-amine-tailed ODNs. More specifically, 3'-amine-tailed 11-mer ODNs having a sequence complementary to the initiation codon region of mRNA corresponding to Hepatitis B surface antigen protein were prepared. Such 3'-tailed ODNs that possess improved target nucleic acid binding properties may be advantageously used as "antisense" oligonucleotides.

C. A Modified Support for Synthesis of 3'-Amine-Tailed ODNs

A further aspect of the present invention provides an improved solid support for synthesis of 3'-amine-tailed ODNs, as shown in Scheme VI. A particularly preferred support in this regard is aminohexyl-modified CPG (AH-CPG), prepared using 6-aminohexan-1-ol.

At present, modification of the 3'-terminus of ODNs may be performed using a commercially available support (for instance, "Amine-ON-CPG" by ClonTech Laboratories, Inc., Palo Alto, Calif.). However, as noted above, such supports (corresponding to the support described by Nelson et al., supra) have significant attendant disadvantages, including production of at least two distinct 3'-tailed ODN products ($\approx$1:1) by PAGE analysis. In addition, derivatization of the 3'-amine tail with various active esters consistently results in poor yields, and HPLC analysis indicates that less than 50% of the starting 3'-amine-tailed ODN reacts.

The suggested mixed products may be a result of: (1) O to N migration of the phosphate moiety of the first nucleotide during synthesis of ODN on the commercial solid support; (2) deprotection of the FMOC moiety of the tail and subsequent capping by acetic anhydride during ODN synthesis; and/or (3) formation of a cyclic phosphate between the primary and secondary hydroxyl group of the tail with concomitant loss of the ODN. In all cases, the resultant 3'-tailed ODN would be subsequently unreactive with active esters and would produce distinct species upon PAGE analysis.

The modified solid support herein overcomes these disadvantages associated with commercially available solid supports for 3'-terminus modification of ODNs. Additional advantageous characteristics provided by the claimed modified solid supports include: (1) a unique amine-protecting group that also functions as the site of CPG attachment; and (2) a dimethoxytrityl-protected hydroxyl group. Moreover, these modified supports are compatible with all procedures used with commercially available DNA synthesizers.

The 3' amine-tailed ODN is preferably removed from the CPG support off the DNA synthesizer. Since the claimed supports do not possess a vicinal diol, release of the 3'-amine tailed ODN from the support with ammonium hydroxide is compatible with preservation of the aminohexyl group at the 3' terminus of the ODN. In contrast, amine-ON-CPG contains a vicinal diol, and release of ODN from this support using ammonium hydroxide results in significant loss of tail molecules from the ODN.

U. Asseline and N. T. Thuong, Tet. Lett. 31:81–84 (1990) reported a solid support for introduction of a 3'-aminohexyl tail onto an ODN. Disadvantages associated with this solid support include: (1) a 7-step synthetic method for making the support (as compared to the 4-step method described herein); (2) analysis of the data suggests that very poor yields of solid support are obtained by the reported method; and (3) the absence of data that suggest that this solid support provides reasonable yields of 3'tailed ODNs.

In addition to the preferred 6-aminohexan-1-ol reagent for making the claimed solid support, other aminoalkanols are commercially available and suitable for production of modified CPG according to the present invention. By substituting aminoalkanols with various alkyl chain lengths for 6-aminohexan-1-ol, ODNs having 3'-amine tails of various lengths may be synthesized by the methods of the disclosure herein. In contrast, aminodiols of varying lengths are not generally commercially available, and thus solid supports having a range of alkyl chain lengths cannot be readily produced according to the method and support of Nelson et al. Accordingly, ODNs having varying 3'-amine tails cannot be easily synthesized using amine-ON-CPG or modifications thereof. Further, other spacer groups (i.e., wherein "R" is alkyl, aryl, arylalkyl, heteroalkyl or heteroaryl) may be inserted between the amino group and DMTr-protected hydroxyl group of the claimed modified solid support. In a preferred embodiment, R is $(CH_2)_n$ and n=1–10. In a particularly preferred embodiment, R is $(CH_2)_6$.

Oligonucleotides having a 3'-amine tail can be efficiently synthesized using the modified solid support of the present invention. Such 3'-amine-tailed oligonucleotides were compared to analogous 3'-tailed ODNs prepared using the commercially available amine-ON CPG support. An exemplary modified solid support of the claimed invention provided enhanced yield of 3'-amine-tailed ODN as a single product by both HPLC and PAGE. Subsequent derivatization of a 3'-amine-tailed ODN made from the claimed modified solid support proceeded rapidly to completion, and provided quantitative yields of 3'-modified ODN without the need for HPLC purification.

D. Reaction of Acridine TFP Esters with Internal-Amine-Modified ODNs

The present invention provides means to introduce multiple internal intercalating groups into ODNs. Such multiple internal intercalating groups may provide enhanced binding of ODN to target nucleic acid strand(s), but they may have strict topological requirements for effective intercalation. The predicted increase in nucleic acid binding affinity attributable to the intercalating groups may be neutralized or overwhelmed by steric effects that disturb the normal Watson-Crick base pairing in the duplex.

The claimed methods include use of acridine TFP esters to prepare bis-modified ODNs that "sandwich" either one or two base pairs in the mini duplex formed between ODN and target. According to the present disclosure, internally modified ODNs may be designed with linking arms that optimize interaction between intercalating groups and the target nucleic acid strand. For instance, 5-aminopropyl-deoxyuridine groups have been selectively introduced into ODNs, and the effects on $T_m$ of one and two internal acridine modifications examined. For a single internal amine modification, ODNs were reacted with acridine TFP esters 19 or 20 to determine the effect of chain length on binding efficiency ($T_m$). An acridine-modified ODN with a 5 carbon length linking arm increased the $T_m$ by 5.9° C., as compared to an unmodified control, while a 3 carbon length linking arm resulted in a 1.1° C. increase, as compared to the same control. When two internal acridine modifications were examined, an increase in $T_m$ from 45.5° C. (unmodified ODN) to 56.2° C. (bis intercalated ODN) was observed with optimized linker arm lengths. In addition, multiple internal acridine modifications may improve cellular uptake of ODNs and stability of ODNs to nuclease digestion.

E. Improved Stability of 3'-Tailed ODNs in Cell Culture (Hexanol-CPG)

Unmodified ODNs are rapidly degraded by 3'-exonucleases in serum-containing media. Certain chemical modifications of the 3'-terminal phosphodiester bond (i.e., changing the last two internucleotidic phosphodiester bonds to phosphorothioates, phosphoroamidates, or inverted linkages) may significantly improve stability of ODNs to nucleases. Other chemical linkages may provide enhanced nuclease stability, such as α-deoxynucleotide derivatives (C. Cazenave et al., *Nucl. Acids Res.* 15:10507 (1987)) and methylphosphonate derivatives. Since intercalating groups are bulky 3'-substituents, they may also protect the terminal phosphodiester linkage from 3'-exonucleases (E. Uhlmann and A. Peyman, *Chem. Rev.* 90:543 (1990)). For instance, 3'-cholesterol-, 3'-acridine-, and 3'-hexylamine-tailed ODNs have been examined in cell culture assay and demonstrated increased stability in comparison to unmodified ODNs.

In one embodiment of the present invention, a method for synthesizing oligonucleotides that resist degradation by 3'-exonucleases using a modified solid support is described. This modified solid support may be advantageously used to synthesize ODNs that do not contain other 3'-modifications and to synthesize ODNs useful for in vivo evaluation of structure-activity relationships of other 3'-modifications, such as cholesterol or acridine. Since 3'-modified ODNs made according to this method do not interfere with hybridization, the modified solid support herein described is a suitable substitute for immobilized DMTr-protected nucleosides that are currently used for ODN synthesis. Disadvantages associated with these immobilized nucleosides include expense and the need to have four types of CPG available. In contrast, within the claimed method the 3'-terminal nucleoside is added as a phosphoramidite, thus the modified solid support may be used as a universal reagent for preparation of any ODN sequence. In addition, the DMTr-protected hydroxyl on the arm protruding from the solid support is unhindered, in contrast to the DMTr-protected 5'-hydroxyl of the immobilized nucleoside. Therefore, the DMTr-protected hydroxyl of the modified solid support displays enhanced accessibility to bulky phosphoramidite reagents and may provide higher yields of ODN product.

The modified solid support of this aspect of the invention features an "R" group (i.e., alkyl, aryl, arylalkyl, heteroalkyl, or heteroaryl) that connects support and DMTr-protected hydroxyl. In a preferred embodiment, R is $(CH_2)_n$ and $n=2-10$. In a particularly preferred embodiment, R is $(CH_2)_6$. Preparation of an exemplary modified solid support, hexanol-CPG, is shown in Scheme VII. The key intermediate in the synthesis of hexanol-CPG, O-(4,4'-dimethoxytrityl)-1,6-hexanediol 37, is prepared by treatment of hexanediol with DMTr-Cl, using a modification of the procedure of F. Seela and K. Kaiser, *Nucl. Acids Res. Res:* 3113 (1987). Succinylation of the intermediate and subsequent immobilization to long chain alkyl amine-controlled pore glass support (LCAA-CPG) yields hexanol-CPG.

3'-hexanol-tailed "antisense" oligodeoxynucleotides have been studied in a model biological system. These antisense ODNs demonstrated a notable effect on swimming behavior of *Paramecium tetraurelia*. Wild-type cells and cells treated with a random or "sense" ODN demonstrated no effect.

The following illustrative examples correlate to the reaction sequences of Schemes I-VIII. In Schemes I and III, the identifier "chol" indicates a cholesteryl moiety. Scheme I shows synthesis of cholesterol-CPG 6; Scheme II describes synthesis of acridine-CPG 10; Scheme III illustrates synthesis of cholesterol-CPG 17; Scheme IV depicts synthesis of acridine TFP esters 19 and 20; Scheme V shows an improved method of synthesizing acridine-CPG be and 23; Scheme VI describes synthesis of aminohexyl-CPG 30; Scheme VII illustrates synthesis of hexanol-CPG 38; and Scheme VIII depicts structures of 3'-acridine tails.

EXAMPLE I

(2S,4R)-N-Benzyloxycarbonyl-4-hydroxy-2-hydroxymethylpyrrolidine (1)

To an ice cold solution of 4.76 g (18 mmoles) of CBZ hydroxyproline (Sigma Chemical Co.) in 20 mL of dry THF was added 45 mL of a 1M solution borane-THF complex in THF (Aldrich). After stirring under argon for 15 min at 0°–5° C., and 4.5 h at room temperature, the mixture was quenched with 50 mL of methanol. After 30 min, the solution was concentrated. The residual colorless syrup was purified by flash chromatography (3.5×23 cm silica) using a gradient of methanol in methylene chloride. The product eluted with 10% methanol. The fractions containing pure product were stripped of solvent to give 2.18 g (46% yield) of 1 as a colorless syrup.

TLC (95:5/methylene chloride:methanol), $R_f=0.16$.

IR (neat) 3600–3100 (br), 2940, 1680, 1420 and 1355 $cm^{-1}$.

$^1H$ NMR (CDCl$_3$) 7.36 (s,5H), 5.17 (s, 2H), 4.50 (m, 2H), 3.67 (m,4H), 2.09 (m, 3H).

Anal. Calcd for $C_{13}H_{17}NO_4 \cdot 0.3H_2O$: C, 60.83; H, 6.91; N, 5.46. Found: C, 60.85; H, 6.88; N, 5.36.

EXAMPLE II

(2S,4R)-4-Hydroxy-2-hydroxymethylpyrrolidine (2) {trans-4-hydroxy-L-prolinol}

A solution of 1.92 g (7.6 mmoles) of CBZ hydroxyprolinol 1 in 50mL of methanol was stirred with 320 mg of 10% Pd on carbon under a balloon of hydrogen. After 16 h, no starting material remained as evidenced by TLC (9:1/methylene chloride:methanol). The mixture was filtered through Celite (washed with methanol) and the filtrate was concentrated to give the desired product 2 as an amber syrup in quantitative yield. The syrup was dissolved in ethanol to give 15.2 mL of a 0.5M stock solution.

IR (neat) 3600–3100 (br), 2920, 1530 and 1410cm$^{-1}$.

$^1H$ NMR (D$_2$O) 4.40 (m, 1H), 3.60 (m, 3H), 3.02 (d of d, 1H, J = 12.4, 4.8 Hz), 2.77 (d of t, 1H, J=12.4, 1.8 Hz), 1.84 (m, 1H), 1.60 (m, 1H0).

EXAMPLE III

(2S,4R)-N-Cholesteryloxycarbonyl-4-hydroxy-2-hydroxymethyl pyrrolidine (3)

To 7.6 mL (3.8 mmoles) of a 0.5M stock solution of hydroxyprolinol 2 in ethanol was added a solution of 1.48 g (3.3 mmoles) of cholesterol chloroformate in 8 mL of methylene chloride. The solution was stirred at room temperature for 1.5 h. The cloudy solution was poured into 100 mL of ice water and the heterogeneous mixture was extracted with 3×150 mL of hot ethyl acetate. The combined organics were washed with brine, dried over magnesium sulfate and concentrated. The solid residue was purified by flash chromatography (4×15cm silica) using a gradient of methanol in 1:1/hexanes:ethyl acetate. The product eluted with 10% methanol. The fractions containing pure product were stripped of solvent to give 1.42 g (81% yield) of 3 as a white solid.

TLC (95:5/methylene chloride:methanol), $R_f=0.10$.
Product stained black upon spraying with 10% sulfuric acid in methanol and heating.
Anal. Calcd for $C_{33}H_{55}NO_4$:C, 74.81; H, 10.46; N, 2.64. Found: C, 74.74; H, 10.33; N, 2.50.

EXAMPLE IV (2S,4R)-N-cholesteryl oxycarbonyl-4-hydroxy-2-dimethoxytrityloxymethylpyrrolidine (4)

To a stirred solution of 1.42 g (2.68 mmoles) of the diol 3 in 27 mL of dry pyridine was added 0,524 mL of triethylamine, 16.5 mg of 4-dimethyl aminopyridine, and 1.10 g (3.23 moles) of dimethoxytrityl chloride. After stirring under argon for 4.5 h, the mixture was stripped of solvent. Residual pyridine was removed by co-evaporation with toluene. The residue was partitioned between 100 mL of ether and 40 mL of water. The aqueous layer was extracted with 80 mL of ether and the combined organic layers were washed with brine, dried over sodium sulfate, and concentrated. The residue was purified by flash chromatography (4.5×20cm silica) using a gradient of ethyl acetate in hexanes. The product eluted just after a yellow impurity with 2:1/hexanes:ethyl acetate. The fractions containing pure product were stripped of solvents to give 1.33 g (60% yield) of 4 as a pale yellow solid foam.

TLC (95:5/methylene chloride:methanol), $R_f=0.49$.
Product stained orange upon spraying with 10% sulfuric acid in methanol.
$^1$H NMR (CDCl$_3$) 7.26 (m, 9H), 6.81 (d, 4H, J=8.8 Hz), 5.30 (m, 1 H), 4.50 (m, 2H), 4.15 (m, 1 H), 2.78 (s, 6H), 2.7–3.0 (m, 4H), 2.4- 0.6 (m, 46H).
Anal. Calcd for $C_{54}H_{73}NO_6$: C, 77.94; H, 8.84; N, 1.68. Found: C, 77.26; H, 8.82; N, 1.56.

EXAMPLE V (2S,4R)-N-cholesteryloxycarbonyl-4-succinyloxy-2-dimethoxy trityloxymethylpyrrolidinone (5)

To a stirred solution of 1.22 g (1.47 mmoles) of the alcohol 4 in 12 mL of dry pyridine was added 443 mg (4.43 mmoles) of succinic anhydride and 89 mg (0.73 mmoles) of dimethylaminopyridine. The mixture was stirred under argon for 26 h and stripped of solvent. Residual pyridine was removed by co-evaporation with toluene. The residue was dissolved in 40 mL of chloroform, washed with brine, dried over sodium sulfate and concentrated to give quantitative yield of the product 5 as a beige solid foam.

TLC (95:5/methylene chloride:methanol), $R_f=0.32$.
Product stained orange upon spraying with 10% sulfuric acid in methanol.

EXAMPLE VI

Cholesterol-CPG support (6)

The succinylated cholesterol derivative 5 was immobilized to long chain alkyl amine-controlled pore glass support (LCAA-CPG, Sigma) using a published procedure (R. T. Pon et al., Biotechn. 6:768 (1988)). LCAA-CPG (5.0 g) was stirred for 3 h with 100 mL of 3% dichloroacetic acid in methylene chloride. The CPG was filtered on a 30 mL sintered glass funnel and washed with 150 mL of chloroform and 150 mL of ether. The solid was dried under vacuum and combined in a 250 mL round bottom flask with 50 mL of dry pyridine, 932 mg (1 mmole) of the succinylated cholesterol derivative 5, 0.4 mL of triethylamine, 1.92 g (10 mmoles) of 1-ethyl-3-(3-dimethylaminopropyl)carbodiimide, and 60 mg of 4-dimethylaminopyridine. The mixture was swirled on an orbital mixer at 100rpm for 38 h. The CPG was filtered on a 30 mL sintered glass funnel and washed with 50 mL pyridine, 100 mL of methanol, 50 mL of chloroform and 50 mL of ether, then dried under vacuum. Residual amine groups on the CPG were capped by swirling the support in 15 mL of dry pyridine and 2.0 mL of acetic anhydride. After 2 h, the CPG was filtered and washed as described above and dried under vacuum to give 5.0 g of the product 6. This material was analyzed for dimethoxytrityl content according to the published procedure (T. Atkinson and M. Smith, in Oligonucleotide Synthesis, a Practical Approach, Gait, M. J. (ed.), IRL Press, (1984), p. 48), and found to have a loading of 17.6 micromoles/gram of CPG support.

EXAMPLE VII

Synthesis of a 3' cholesterol tailed oligonucleotide from cholesterol-CPG

A quantity of cholesterol-CPG corresponding to 1 micromole of dimethoxytrityl content was packed into an empty column, e.g., an Applied Biosystems Inc. or Cruachem column. An oligonucleotide with the base sequence CTCCATGTTCGTCACA was prepared on a Milligen DNA synthesizer using standard phosphoramidite chemistry. The 5'-DMTr protecting group was left on. The oligonucleotide was cleaved from the CPG and deprotected by treatment with 2 mL of concentrated ammonia at room temperature for 3 days. The supernatant was injected directly on a PRP-1 reverse phase HPLC column (elution with a gradient of 20% acetonitrile to 100% acetonitrile in pH 7.5 triethylammonium acetate). The product was collected in one fraction and lyophilized to give the 5'-DMTr protected product. The DMTr group was removed by treatment with 80% acetic acid (16 h at room temperature) and repurified by HPLC. The collected product was analyzed by UV at 260 nm and found to contain 0.54 mg of product. In an alternate iteration of this procedure, the DMTr group was removed while on the synthesizer with 3% DCA to give an increased yield of the oligonucleotide.

EXAMPLE VIII (2S,4R)-N-(9-acridinepropanamidyl)-4-hydroxy-2-hydroxymethylpyrrolidine (7) {1- [3-(9-Acridinyl)-1-oxopropyl]-5-hydroxymethyl-(3R-trans)-3-pyrrolidinol; Scheme II}

To a stirred slurry of 125.5 mg (0.5 mmoles) of 9a-cridinepropionic acid (H. Jensen and L. J. Howland, Am. Chem. Soc. 48:1926 (1989)) and 0.104 mL (0.6 mmoles) of ethyldiisopropylamine in 15 .mL of methylene chloride was added 0.6 mmoles of 2-fluoro-1-methylpyridinium rosylate (FMPT). After 1.5 h at room temperature, the cloudy brown solution was added to a stirred solution of 0.5 mmoles (1.5L) of hydroxy prolinol 2 in ethanol in an ice-salt bath. After stirring for 1 h at room temperature, the mixture was quenched with 10 mL of methanol and concentrated. The residue was purified by flash chromatography (1.5×24 cm silica) using a gradient of methanol in methylene chloride. The fractions that contained pure product were stripped of solvent to give 112 mg (64% yield) of 7 as a yellow solid foam.

TLC (90:10/methylene chloride:methanol), $R_f$=0.50. Product appeared as a yellow spot with blue fluorescence.

IR (KBr) 3400 (br), 1620, 1440, 1070 cm$^{-1}$.

$^1$H NMR (CDCl$_3$) 8.30 (d, 4H, J=9.4 Hz), 7.82 (t, 2H, J=6.6 Hz), 7.62 (m, 2H), 4.31 (m, 2H), 4.05 (t, 2H, J=8.2 Hz), 3.70 (m, 1H), 3.50 (m, 2H), 3.22 (d, 2H, J=1.4 Hz), 2.78 (m, 2H), 2.03 (m, 1H), 1.64 (m, 1H).

Anal. Calcd for $C_{21}H_{22}N_2O_3.0.5H_2O$: C, 70.18; H, 6.45; N, 7.79. Found: C, 70.41; H, 6.45; N, 7.68.

EXAMPLE IX (2S,4R)-N-(9-acridinepropanamidyl)-4-hydroxy-2-dimethoxy-trityloxymethylpyrrolidine (8)

To a stirred solution of 100 mg (0.285 mmoles) of the diol 7 in 2.5mL of pyridine was added 6.4 mg of 4-dimethylaminopyridine, 0.13 mL of triethylamine and 154 mg of dimethoxytrityl chloride. After stirring for 16 h under argon, the mixture was stripped of solvent. Residual pyridine was removed by co-evaporation with methylene chloride. The residue was dissolved in 5 mL of methylene chloride and washed with 2×3 mL of water and 3 mL of brine, dried over sodium sulfate and stripped of solvent. The residue was purified by flash chromatography (1.5×20 cm silica) using a gradient of methanol in 1:1/hexanes:ethyl acetate. The fractions containing pure product were combined and stripped of solvent to give 123 mg (66% yield) of 8 as a yellow solid foam.

TLC (45:45:10/hexanes:ethyl acetate:methanol), $R_f$=0.26.

Product appeared as a yellow spot with blue fluorescence that stained orange upon spraying with 10% sulfuric acid in methanol.

IR (KBr) 3400 (br), 1620, 1440, 1070 cm$^{-1}$.

$^1$H NMR (CDCl$_3$) 8.17 (m, 4H), 7.75 (t, 2H, J=7.0 Hz), 7.57- 7.09 (m, 9H), 6.82 (d, 2H, J=8.8 Hz), 6.66 (m, 2H), 4.56 (m, 2H), 3.65- 2.90 (m, 2H), 2.69 (m, 2H), 2.15 (m, 1H), 1.95 (m, 1H).

Anal. Calcd for $C_{42}H_{40}N_2O_5.0.5 H_2O$: C, 76.23; H, 6.24; N, 4.23. Found: C, 76.53; H, 6.67; N, 3.80.

EXAMPLE X (2S,4R)-N-(9-acridinepropanamidyl)-4-succinyloxy-2-dimethoxy-trityloxymethylpyrrolidine (9)

To a stirred solution of 120 mg (0.184 mmoles) of the alcohol 8 in 1.5 mL of dry pyridine was added 55.5 mg (0.55 mmoles) of succinic anhydride and 11.2 mg of 4-dimethylaminopyridine. The mixture was stirred under argon for 40 h and stripped of solvent. Residual pyridine was removed by co-evaporation with toluene. The residue was dissolved in 3 mL of chloroform, washed with brine, dried over sodium sulfate and concentrated to give 128 mg (93% yield) of the product 9 as a yellow solid foam.

TLC (95:5/methylene chloride:methanol), $R_f$=0.13. Product appeared as a yellow spot with blue fluorescence that stained orange upon spraying with 10% sulfuric acid in methanol.

EXAMPLE XI

Acridine-CPG support (10)

The succinylated acridine derivative 9 was immobilized to a long chain alkyl amine-controlled pore glass support using the procedure described above for the cholesterol-CPG support 6. Acid washed LCAA-CPG (0.85 g) was combined in a round bottom flask with 8.5 mL of dry pyridine, mg (0.170 mmoles) of the succinylated acridine derivative 9, 0.068 mL of triethylamine, 325 mg (1.7 mmoles) of 1-ethyl-3-(3-dimethylaminopropyl)-carbodiimide, and 10.2 mg of 4-dimethylaminopyridine. The mixture was stirred under argon for 19 h. The CPG was filtered off and washed with pyridine, methanol, chloroform and ether, then dried under vacuum. Residual amine groups on the CPG were capped by stirring the support in 2.5 mL of dry pyridine and 0.34 mL of acetic anhydride. After 2 h, the CPG was filtered and washed as described above and dried under vacuum to give 0.85 g of the product 10. This material was analyzed for dimethoxytrityl content found to have a loading of 18.5 micromoles/gram of CPG support.

EXAMPLE XII

Synthesis of a 3'-acridine-tailed oligonucleotide from acridine-CPG

A quantity of acridine-CPG 10 corresponding to 1 micromole of dimethoxytrityl content was packed into an oligonucleotide synthesis column. An oligonucleotide with the base sequence 5'-CTCTCCATCTTCGT-CACA was prepared on a Milligen DNA synthesizer using standard phosphoramidite chemistry. The 5'-DMTr protecting group was removed on the synthesizer. The oligonucleotide was cleaved from the CPG and deprotected by treatment with 2 mL of concentrated ammonia at 40° C. for 24 h. The supernatant was injected directly on a PRP-1 reverse phase HPLC column (elution with a gradient of 20% acetonitrile to 100% acetonitrile in pH 7.5 triethylammonium acetate). The product 10' was collected in one fraction and lyophilized to give 1.99 mg (determined by UV at 260 nm) of the fluorescent oligonucleotide product as a pale yellow solid.

EXAMPLE XIII

4-N-Benzyloxycarbonyl-3-hydroxybutyric acid (11)

5.0 g (42.0 mmoles) of 4-amino-3-hydroxybutyric acid (Sigma Chemical Co.) was dissolved in a solution of 3.7 g of sodium hydroxide in 35 mL of water. The solution was cooled in ice and 7.88 g (46.2 =moles) of CBZ chloride was added dropwise over 20min. The mixture was stirred in ice for 2 h, then washed with 50 mL of ether to remove excess CBZ chloride. The aqueous layer was acidified with 20 mL of 3N HCL and extracted with 4×50 mL of ethyl acetate. The combined extracts were dried over magnesium sulfate and the solvent was removed at reduced pressure to give a colorless syrup which started to crystallize. Recrystallization from chloroform gave 4.70 g (44% yield) of the desired product 11 as white crystals (mp=94°-95° C.).

$^1$H NMR (CDCl$_3$) 7.35 (s, 5H), 6.70 (s, 2H), 5.70 (s, 1H), 5.15 (s, 2H), 4.35- 3.95 (m, 1H), 3.25-3.00 (m, 2H), 2.50 (d, 2H, J=6.5 Hz).

EXAMPLE XIV

1-N-Benzyloxycarbonyl-2,4-butanediol (12)

4.57 g (18.0 mmoles) of the acid 11 in 18 mL of dry THF was added dropwise with stirring to an ice cold solution of 1M borane-THF in THF (Aldrich Chemical Co.) under a blanket of argon. After the addition was complete, the mixture was stirred at room temperature for 30min and then quenched with 36 mL of 10% acetic acid in methanol. The solvent was removed at reduced pressure and the residue was taken up in 80 mL of ethyl acetate and washed with 1.5N HCl, water and sat. sodium bicarbonate. After drying over potassium carbonate, the solvent was removed at reduced pressure to give a white solid. Recrystallization from benzene/hexanes gave 1.69 g (39% yield) of the desired product 12 as white crystals (mp=80.5°-82° C.).

$^1$H NMR (CDCl$_3$) 7.35 (s, 5H), 5.50 (t, 1H, J=6.0 Hz), 5.10 (s, 2H), 3.75 (t, 2H J=6.0), 4.10-2.65 (m, 5H), 1.60 (q, 2H, J=6.0 Hz).

EXAMPLE XV

1-Amino-2,4-butanediol (13)

Scheme III: 1.69 g (7.06 mmoles) of the CBZ protected aminodiol 12 was combined with 800 mg of Pd(OH)$_2$ on carbon, 100 mL of ethanol and 20 mL of 1,4-cyclohexadiene and the mixture was refluxed for 16 h. TLC (10% methanol in methylene chloride) showed no remaining starting material. The mixture was filtered through Celite on a sintered glass funnel (ethanol wash) and the solvent removed at reduced pressure to give 0.84 g of the desired product 13 as an amber syrup. Dilution to 7 mL with ethanol gave a 1M stock solution of the aminodiol 13.

$^1$H NMR (D$_2$O) 4.80 (s, 4H), 3.80 (t, 2H, J: 6.0 Hz), 4.00-3.65 (m, 1H), 3.40-2.50 (m, 2H), 1.95-1.55 (m, 2H).

EXAMPLE XVI

1-N-Cholesteryloxycarbonyl-2,4-butanediol (14)

To an ice cold solution of 6.0 mL (6.0 mmoles) of the aminodiol 13 in ethanol was added a solution of 2.25 g (5.00 mmoles) of cholesterol chloroformate in 5 mL of methylene chloride. The mixture was removed from the ice bath and stirred under argon for 1.5 h, then poured over 150 g ice water. The mixture was extracted with 2×150 mL, ethyl acetate and the extracts were washed with 2×100 mL water, 1×100 mL brine, dried over magnesium sulfate and stripped of solvent. The solid residue was dissolved in 10 mL of THF and chromatographed through a 3.5×15 cm silica gel column (packed with 121 hexanes:ethyl acetate). After elution with 300 mL of 121 hexanes:ethyl acetate, 45:45:10 hexanes:ethyl acetate:methanol was used to sluts the product. Removal of solvent gave 2.04 g (79%) of sticky white solid 14.

$^1$H NMR (CDCl) 5.38 (d, 1H), 5.14 (t, 1H), 4.50 (m, 1H), 4.00-3.70 (m, 3H), 3.60-3.00(m, 2H), 2.40-2.20 (m, 2H), 2.10-0.60 (m, 3H).

EXAMPLE XVII

1-N-Cholesteryloxycarbonyl-2-hydroxy-4-dimethoxytrityloxy butane (15)

To a stirred solution of 1.74 g (3.35 mmoles) of the diol 14 in 25 mL of dry pyridine was added 1.36 g (4.02 mmoles) of dimethoxytrityl chloride, 0.655 mL of triethylamine, and 20.5 mg of 4-dimethylaminopyridine. The reaction mixture was stirred for 16 h under argon, then partitioned between 25 mL of water and 75 mL of ether. The aqueous layer was extracted with another 75 mL of ether and the combined extracts were washed with water and brine, then dried over sodium sulfate and stripped of solvents. The residue was chromatographed through a 3.5×13 cm silica gel column (packed with 421 hexanes:ethyl acetate). The fractions containing product (contaminated with a yellow impurity were combined and stripped of solvent giving 2.22 g of yellow solid foam. Repeated chromatography using 5% methanol in methylene chloride and 4:1 hexanes:ethyl acetate gave the pure product 15 as a pale yellow solid foam.

$^1$H NMR (CDCl$_3$) 7.45-7.10 (m, 9H), 6.80 (d, 4H, J=8.8 Hz), 5.38 (d, 1H), 5.05 (br t, 1H), 4.50 (m, 1H), 3.90-3.80 (m, 2H), 3.80 s, 6H), 3.50-2.95 (m, 4H), 2.30 (m, 2H), 2.10-0.60 (m, 43H).

Anal. Calcd for C$_{33}$H$_{73}$NO$_6$: C, 77.62; H, 8.97; N, 1.17. Found: C, 77.41; H, 8.97; N, 1.60.

EXAMPLE XVIII

1-N-Cholesteryloxycarbonyl-2-succinyloxy-4-dimethoxytrityloxy butane (16)

To a stirred solution of 415 mg (0.506 mmoles) of the alcohol 15 in 2 mL of dry pyridine was added 30 mg of 4-dimethylaminopyridine and 48 mg (0.48 mmoles) of succinic anhydride. The mixture was stirred under argon for 24 h. TLC (5% methanol in methylene chloride) indicated a trace of unreacted starting material. The mixture was stripped of solvent and residual pyridine was removed by co-evaporation with toluene (2×10 mL). The residual yellow solid foam 16 was used for conversion to the p-nitrophenyl ester and immobilization to CPG.

EXAMPLE XIX

Cholesterol-CPG support (17)

The succinylated cholesterol derivative 16 was immobilized to long chain alkyl amine-controlled pore glass support (LCAA-CPG, Sigma) using the procedure of Atkinson and Smith (1984) in *Oligonucleotide Synthesis, a Practical Approach*, Gait, M. J. (ed.) IRL Press, pp 47–49. 105 mg of the crude succinate 16 was dissolved in 1.0 mL of dry dioxane along with 16 mg p-nitrophenol and 0.05 mL dry pyridine. Dicyclohexylcarbodiimide (52 mg, 0.25 mmoles) was added and the mixture was stirred for 15min at room temperature and cooled in a refrigerator for 16 h. The crude p-nitrophenyl ester solution was filtered through a small pad of Celite to remove DCU and the filtrate was added directly to 0.50 g of LCAA-CPG in 1.5 mL of DMF. 0.1 mL of ethyl diisopropylamine was added and the mixture was stirred for 18 h under argon. The CPG was filtered on a sintered glass funnel and washed with 3×10 mL of DMF, 3×10 mL of methanol and 3×10 mL of ether. The derivatized CPG was dried on a vacuum pump and "capped" by treatment with 1.5 mL of dry pyridine and 0.2 mL of acetic anhydride. After stirring for 3 h under argon, the CPG was filtered and washed with 3×10 mL of methanol and 3×10mL. of ether. Drying on a vacuum pump gave 0.46 g of cholesterol-CPG 17. The CPG was analyzed for DMTr content according to the protocol described in Gait and found to have a loading of 24 micromoles/gram of CPG support.

EXAMPLE XX

Synthesis of 3'-cholesterol-tailed 5'DMTr-thymidine from cholesterol-CPG 17

To test the suitability of cholesterol-CPG 17 for oligonucleotide synthesis, a single thymidine residue was added to 41.6 mg (1 micromole) of the solid support. A Milligen DNA. synthesizer was used along with standard phosphoramidite coupling chemistry. The 5'-dimethoxytrityl protecting group on the thymidine was not removed in order to aid in isolation and characterization of the product. The CPG was washed well with acetonitrile (SmL) in order to eliminate trace amounts of unreacted DMTr-thymidine phosphoramidite and other non-covalently attached impurities. The CPG was dried on a vacuum pump and analyzed for DMTr content as described above, and found to have a loading of 27 micromoles/gram. The 3'-cholesterol tailed thymidine was cleaved from 20 mg of the support by 24 h treatment with 10 mL of concentrated ammonia at 44° C. in a 5 mL Reactivial (Teflon liner). The 3'-cholesterol tailed thymidine was isolated by removing the supernatant (pasteur pipet) and washing the support with 3×2 mL of methanol. The combined washings were stripped of solvent (rotovap/vacuum pump) and analyzed by thin layer chromatography on silica gel plates using 7:1:1:1:1 ethyl acetate:acetone: methanol:water:acetic acid. One major DMTr containing spot ($R_f=0.63$) stained orange upon spraying with 10% sulfuric acid in methanol. Only trace amounts of DMTr-thymidine ($R_f=0.84$) could be detected, thus indicating the stability of the cholesterol linkage. The CPG support after ammonia treatment for 24 h had a DMTr content of 1.4 micromoles/gram.

Ammonia treatment of DMTr-thymidine derivatized cholesterol-CPG for only 5 h at 44° C. gave TLC results which were similar to the 24 h treatment. The CPG support after 5 h of ammonia treatment had a DMTr content of 3.2 micromoles/gram.

The oligonucleotide 10' from Example XII, bearing an acridine 3'-tailed molecule thereon, was studied as to its melting temperature characteristics in the presence of a complementary oligonucleotide strand. The presence of the acridine intercalating agent raised the $T_m$ approximately 4° C., in comparison to a similar oligonucleotide that did not bear a 3'-tailed acridine molecule.

Appropriate reporter groups attached to the 3' tail of appropriate oligonucleotides are useful for identifying the presence of the oligonucleotide. Fluorescence, chemiluminescence or other properties of such reporter groups serve to nonradioactively "tag" these nucleotides. The nucleotides can then be identified in a sample of interest, as for instance a biological sample, by the presence of fluorescence or other like property. A lipophilic tail group, as for instance a cholesterol tailed 3' oligonucleotide, assists in the transfer of the oligonucleotide across the cell membrane. Thus, increased concentration of the oligonucleotide within the cell or facilitated transfer of the oligonucleotide across the cell membrane is achieved. A cleaving group on the 3' tail of the oligonucleotide can assist in site specific cleavage of DNA bearing the oligonucleotide's complementary sequence after binding of the oligonucleotide to such complementary sequence. Such use might be implicated in gene identification, isolation and the like.

Other "tail molecules" or "conjugates" might be selected based on other properties both biological and physical. Such other biological tail molecules might include appropriately blocked synthetic peptides, puromycin, digoxigenin and the like. Other tail molecules having useful physical properties might include spinlabeled compounds, DTPA chelating agents, phospholipids, di- and trinitrophenyl groups and cross-linking agents including alkylating agents, azidobenzenes, psoralen, iodoacetamide, azidoproflavin and azidouracil.

EXAMPLE XXI

2,3,5,6-Tetrafluorophenyl trifluoroacetate (18)

Trifluoroacetic anhydride (28 mL, 0.2 mol) was added dropwise with stirring to 27.1 g (0,163 mol) of 2,3,5,6tetrafluorophenol. Boron trifluoride etherate (0.2 mL) was added and the mixture was refluxed overnight. The residual solution was distilled at atmospheric pressure to remove trifluoroacetic anhydride and trifluoroacetic acid. The desired product 18 (32.2 g; 75% yield) was collected at 45° C. (18mm) as a colorless liquid:

d=1.52 g/mL

IR (CHCl$_3$) 3010, 1815, 1525, 1485, 1235, 1180, 1110, 955 cm$^{-1}$.

Anal. Calcd for $C_8HO_2F_7$: C, 36.66; H, 0.38; F, 50.74. Found: C, 36.31; H, 0.43; F, 50.95.

EXAMPLE XXII

2,3,5,6-Tetrafluorophenyl 3-(9-Acridinyl)propionate (19)

Method a: To a solution of 400 mg (1.59 mmol) of 3-(9-acridinyl)propionic acid and 0.22 mL of triethylamine in 20 mL of methylene chloride was added 496 mg (1.75 mmol) of 2-fluoromethylpyridinium tosylate (FMPT). The mixture was stirred at room temperature for 15 min. 317 mg (1.91 mmol) of 2,3,5,6-tetrafluorophenol and 0.22 mL of triethylamine were added and the mixture was stirred for 15 min. The heterogeneous mixture was stripped of solvents and the residue was purified by flash chromatography (2×29 cm silica) using 1:1 hexanes:ethyl acetate. The fractions containing pure product were combined and evaporated to dryness to give 250 mg (39% yield) of the desired product 19 as a pale yellow solid:

$^1$H NMR (CDCl$_3$) 8.26 (d, 4H, J=9.2 Hz), 7.92 (t, 2H, J=6.8 Hz), 7.58 (t, 2H, J=8.8 Hz), 7.00 (m, 1H), 3.71 (t, 2H, J=7.8 Hz), 2.78 (t, 2H, J=6.4 Hz), 2.05 (m, 4H).

Anal. Calcd for C$_{24}$H$_{17}$NO$_2$F$_4$: C, 67.45; H, 4.01; N, 3.28; F, 17.78. Found: C, 67.18; H, 3.87; N, 3.02; F, 17.67.

EXAMPLE XXIV

1-[3-(9-Acridinyl)-1-oxopropyl]-5-hydroxymethyl-(3R-trans)-3-pyrrolidinol (7)

Scheme V: A solution of 206 mg (0.52 mmol) of the acridine TFP ester 19 in 8 mL of methylene chloride was added dropwise to an ice cold solution of 0.57 mmol of the aminodiol 2 and 86 μL of triethylamine in 1.14 mL of ethanol. The mixture was stirred at room temperature for 18 h and concentrated. The residue was purified by flash chromatography (1.5×25 cm silica) using 5% methanol in methylene chloride to give 181 mg (100% yield) of the desired product 7 as a yellow solid foam:

TLC (9:1 methylene chloride:methanol), $R_f$=0.50, yellow spot with blue fluorescence under long wavelength UV;

IR (KBr) 3400 (br), 1620, 1440 and 1070 cm$^{-1}$;

$^1$H NMR (CDCl$_3$) 8.30 (d, 4H, J=9.4 Hz), 7.82 (t, 2H, J=6.6 Hz), 7.62 (m, 2H), 4.31 (m, 2H), 4.05 (t, 2H, J=8.2 Hz), 3.70 (m, 1H), 3.50 (m, 2 H), 3.22 (d, 2H, J=1.4 Hz), 2.78 (m, 2H), 2.03 (m, 1H), 1.64 (m, 1H).

Anal. Calcd for C$_{21}$H$_{22}$N$_2$O$_3$.0.5 H$_2$O: C, 70.18; H, 6.45; N, 7.79. Found: C, 70.41; H, 6.45; N, 7.68.

UV (pH 7.2) $\lambda_{max}$=252 nm ($\epsilon$ 101,000), 260 nm ($\epsilon$6400), 356 nm ($\epsilon$6200).

Fluorescence (pH 7.2) excitation at 355 nm, emission at 460 nm.

mp=183°–185° C.;

TLC (1:1 hexanes:ethyl acetate), R$_f$=0.70, blue fluorescence under long wavelength UV;

IR (KBr) 3075, 1790, 1520 and 1095 cm$^{-1}$;

$^1$H NMR (CDCl$_3$) 8.29 (d, 4H, J=8.0 Hz), 7.82 (t, 2H, J=7.2 Hz), 7.64 (t, 2H, J=8.6 Hz), 7.04 (m, 1H), 4.13 (t, 2H, J=8.7 Hz), 3.16 (t, 2H, J=8.7 Hz).

Anal. Calcd for C$_{22}$H$_{13}$NO$_2$F$_4$: C, 66.17; H, 3.28; N, 3.51; F, 19.03. Found: C, 66.01; H, 3.11; N, 3.33; F, 19.13.

Method b: To a stirred slurry of 251 mg (1 mmol) of 3-(9-acridinyl)propionic acid in 10 mL of methylene chloride was added 200 μL (1.4 mmol) of triethylamine and 200 μL of TFP trifluoroacetate 18. After stirring the mixture under argon for two days, the heterogeneous mixture was filtered through Celite and the filtrate was evaporated to dryness. The residue was purified by flash chromatography (2×25 cm silica) using 1:1 hexanes:ethyl acetate. The fractions containing product were combined and evaporated to dryness. The residue was repurified by flash chromatography (2×25 cm silica) using methylene chloride. The pure product eluted as a yellow band with 5% ethyl acetate in methylene chloride. The fractions containing pure product were combined and evaporated to dryness to give 67 mg (17% yield) of 19 as a pale yellow solid.

EXAMPLE XXIII 2,3,5,6-Tetrafluorophenyl 5-(9-Acridinyl)pentanoate (20)

A procedure similar to Example XXII, method a (described above) was used for preparation of 20. 262 mg (1 mmol) of 5-(9-acridinyl) pentanoic acid gave 180 mg (42% yield) of 20 as a pale yellow solid:

mp=122°–124° C.;

TLC (1:1 hexanes:ethyl acetate), R$_f$=0.63, blue fluorescence under long wavelength UV;

IR (KBr) 3075, 2960, 1790, 1515, 1105, 955 and 750 cm$^{-1}$;

EXAMPLE XXV

1-[5-(9-Acridinyl)-1-oxopentyl]-5-hydroxymethyl-(3R-trans)-3-pyrrolidinol (21)

A procedure similar to that described in Example XXIV was used for the preparation of 21. 1.28 g (3.00 mmol) of acridine TFP ester 20 gave 1.04 g (92% yield) of 21 as a pale yellow solid foam:

TLC (45:45:10 hexanes:ethyl acetate:methanol), R$_f$=0.14, yellow spot with blue fluorescence under long wavelength UV;

IR (CHCl$_3$) 3350 (br), 3010, 2930, 1610 and 1435 cm$^{-1}$;

$^1$H NMR (CDCl$_3$) 8.22 (d, 4H, J=9.0 Hz), 7.77 (t, 2H, J=6.6 Hz), 7.56 (t, 2H, J=7.8 Hz), 4.27 (m, 2H), 3.7-3.4 (m, 6H), 2.3-1.6 (m, 10H).

Anal. Calcd for C$_{23}$H$_{26}$N$_2$O$_3$.0.75 H$_2$O: C, 70.48; H, 7.07; N, 7.15. Found: C, 70.33; H, 6.89; N, 7.15.

EXAMPLE XXVI

1-[5-(9-Acridinyl)-1-oxopentyl]-5-[bis(4-methoxyphenyl)phenylmethoxy]methyl-(3R-trans)-pyrrolidinol (22)

A procedure similar to that described in Example IX was used for preparation of 22. 103 mg (0.272 mmol) of the diol 21 gave 78 mg (42% yield) of 22 as a pale yellow solid foam:

TLC (45:45:10 hexanes:ethyl acetate:methanol), R$_f$=0.41, yellow spot with blue fluorescence which stained orange upon spraying with 10% sulfuric acid in methanol;

IR (KBr) 3350 (br), 2930, 1610, 1510 and 1250 cm$^{-1}$;

$^1$H NMR (CDCl$_3$) 8.24 (d, 4H, J=8.8 Hz), 7.76 (m, 2H), 7.53 (m, 2H), 7.35-7.10 (m, 9H), 6.79 (m, 4H), 4.7-4.3 (m, 2H), 4.08 (m, 1H), 3.9-3.3 (m, 11H), 3.10 (m, 2H), 2.32-1.71 (m, 6H).

EXAMPLE XXVII

Acridine-CPG Support (23)

A procedure similar to that described in Examples X and XI was used for preparation of 23. 58 mg (80 μmol) of alcohol 22 and 0.39 g of LCAA-CPG gave 23 with a DMTr loading of 20.6 μmole/g of CPG support.

EXAMPLE XXVIII

Direct Synthesis of 3'-Tailed Oligonucleotides (24–26) Using CPG Supports 6, 10 and 23

3'-Tailed oligonucleotides having a sequence complementary to the initiation codon region of mRNA corresponding to Hepatitis B surface antigen protein (5'-TCCATGTTCGT) were synthesized using CPG supports 6, 10 and 23. Such 3'-tailed ODNs with improved binding properties may be advantageously used as "antisense" oligonucleotides, Synthesis of 3'-tailed oligonucleotides having the sequence 5'-TCCATGTTCGT was performed using solid supports 6 and 10, as described in Examples VII and XII, respectively. Synthesis of the same 3'-tailed oligonucleotide using solid support 23 was analogous to the procedure described in Example XII, except solid support 23 was substituted for solid support 10.

EXAMPLE XXIX

Preparation of 3'-aminohexyl-CPG (AH-CPG)

a. 1,3-Dioxo-2-(6-hydroxyhex-1-yl)-isoindole-5-carboxylic acid (27)

A mixture of 6-aminohexan-1-ol (11.7 g, 10 mmol) and 1,2,4-benzenetricarboxylic anhydride (7.68 g, 4 mmol) was heated to 175°–225° C. for 15 min or until evolution of H$_2$O vapor stops. The melt was poured into water to give a white crystalline solid. The solid was collected by vacuum filtration and dried overnight in vacuo to give 9.1 g (78%) of analytically pure 27.

mp 127°–135° C.;

$^1$H NMR (DMSO-d$_6$): δ 8.344 (1H, d, H-7[6]); 8.208 (1H, s, H-4); 7,967 (1H, d, H-6[7]); 3.578 (2H, t, H-1'[6']); 3.365 (2H, t, H-6'[1']); 1.7-1.2 (8H, m, H-2',3',4',5');

Anal. Calcd for C$_{15}$H$_{17}$N$_1$O$_5$: C, 61.85; H, 5.88; N, 4.81;

Found: C, 61.56; H, 6.12; N, 4.98.

b. 1,3-Dioxo-2-(6-dimethoxytrityloxyhex-1-yl)-isoindole-5-carboxylic acid (28)

To a solution of 27 (2.91 g, 10mmol) in pyridine (50 mL) and triethylamine (1.9 mL) was added dimethoxytrityl chloride (7.11 g, 20 mmol) and 4-dimethylaminopyridine (63 mg). The solution was stirred overnight and then evaporated to dryness. The residue was dissolved in $CH_2Cl_2$ (100 mL). The resulting solution was washed with ice-cold 1M citric acid (100 mL); with $dH_2O$ (100 mL); then dried over $Na_2SO_4$; and then evaporated to a stiff syrup. The syrup 27 was used without further purification.

c. p-Nitrophenyl 1,3-dioxo-2-(6-dimethoxytrityloxyhex-1-yl)-isoindole-5-carboxylate (29)

To a mixture of 28 (2.4 g, 4 mmoles) in $CH_2Cl_2$ was added triethylamine. After cooling the solution in an ice/water bath, p-nitrophenyl chloroformate was added and the solution stirred for 5 h at 4° C. 4-Dimethylaminopyridine was added to the cold solution, and then the solution was allowed to warm to ambient temperature. After stirring overnight at ambient temperature, the solution was repeatedly extracted with sat. $NaHCO_3$ (5×100 mL) and then once with ice-cold 1M citric acid. The organic phase was dried over $Na_2SO_4$ and evaporated to dryness. The residue was flash chromatographed on a silica gel column (29×150 mm) using toluene:EtOAc (5:1) as the eluent. Fractions containing pure material were pooled and evaporated to dryness to give 1.7 g (60%) of analytically pure 29.

Anal. Calcd for $C_{42}H_{38}N_2O_9$: C, 70.58; H, 5.36; N, 3.92;

Found: C, 70.57; H, 5.22; N, 3.84.

d. 3'-Amine CPG Support (AH-CPG) (30)

Long chain alkylamine CPG was activated with 3% dichloroacetic acid in methylene chloride. The activated CPG (1 g) was treated with a solution of 29 (143 mg, 0.2 mmol) in pyridine (10 mL) and $Et_3N$ (1 mL). The reaction mixture was gently agitated for 24 h. The remaining amines were capped by treating with acetic anhydride (0.5 mL) and gently agitating for 24 h. The CPG was filtered, washed with pyridine (1×5 mL), washed with acetonitrile (3×5 mL), and air dried. The AH-CPG 30 was then dried in vacuo for 2 days at ambient temperature. Analysis of the AH-CPG by treatment with perchloric acid indicated a loading of 20 $\mu$mole/g. The AH-CPG support (50 mg, 1 $\mu$mole) was packed into standard 1 $\mu$mole synthesizer columns.

EXAMPLE XXX

Synthesis of Amine-Modified Oligonucleotides (32, 33)

ODNs were prepared from two different CPG supports on a 1 $\mu$mole scale using standard $\beta$-cyanoethyl phosphoramidite coupling chemistry (Atkinson and Smith, supra). AH-CPG 30, prepared as described above in Example XXIX, was used to synthesize 32. "Amine-ON" CPG, obtained from ClonTech Laboratories, Inc. (Palo Alto, Calif.), was used to synthesize 33.

Amine-modified ODNs 32 and 33 having the sequence 5'-TCCATGTTCGT were prepared using either a Milligen 7500 or an Applied Biosystems Model 380B with the protocols supplied by the manufacturer. After ammonia deprotection, the tritylated ODNs were HPLC purified by direct injection of the ammonia solution onto a Hamilton PRP-1 column (305×7.0 mm), and the amine-modified ODN product 32 or 33 was eluted using a linear gradient of 20%–45% acetonitrile in 0.1M TEAA (pH 7.5) over 20 min (flow rate=4 mL/min). Appropriate fractions were combined and concentrated to dryness on a Savant Speed-Vac. The residue was detritylated in 80% acetic acid (500 $\mu$L, 28° C., 70 min), precipitated with 100 $\mu$L of 3M sodium acetate and 4 mL of 1-butanol, centrifuged, washed with 1 mL of ethanol, centrifuged, evaporated to dryness, and reconstituted with 1 mL of sterile distilled water. The concentration of ODN 32 or 33 was determined from the UV absorbance at 260 nm. All ODN concentrations were measured in pH 7.2 PBS (9.2 mM disodium phosphate, 0.8 mM monosodium phosphate, 0.131M sodium chloride). An extinction coefficient for each ODN was determined using a nearest neighbor model (C. R. Cantor et al., Biopolymers 9:1059 (1970)), and used to calculate a theoretical ratio of $A_{260}$ to concentration in $\mu$g/mL. The purified ODN 32 or 33 was analyzed by HPLC on a Dynamax C-18 column (0.75×25 cm) using a linear gradient of 5%–45% acetonitrile in TEAA over 20 minutes (flow rate=1 mL/min). ODN purity was confirmed by denaturing PAGE analysis.

EXAMPLE XXXI

Synthesis of a 3'-Acridine-Tailed ODN (32a)

The 3'-amine-tailed ODN 32 analyzed by analytical C-18 HPLC showed one peak and PAGE showed only one band. Isolated 3'-amine-modified ODN 32 [100 $\mu$g (29 nmol)] was dissolved in 100 $\mu$L water and 50 $\mu$L of 1.0M borate buffer (pH 8.3). 220 $\mu$L of a freshly prepared 5.0 mg/mL solution of acridine TFP ester 19 in 1:1 M-pyrol:acetonitrile (1.1 mg, 3.0 $\mu$mol) was added and the heterogeneous mixture was shaken at room temperature. The progress of the reaction was monitored by HPLC. The reaction of the amine-tailed ODN 32 with acridine TFP ester 19 was complete in less than one hour. In order to more easily separate the 13 min product from a 14 min contaminant, the crude reaction mixture was pre-purified by adding 1.5 mL of water and centrifuging through a 3000 MW cutoff ultrafiltration membrane (Centricon-3 microconcentrator; Amicon) to a final volume of $\approx$100 $\mu$L. This solution was purified by HPLC on a Dynamax C-18 column (0.75×25 cm) using a linear gradient of 5%–45% acetonitrile in 0.1M TEAA over 20 min (flow rate=1 mL/min). The product was collected in one fraction and concentrated on the Speed-Vac. The residue was reconstituted with 100 $\mu$L of sterile distilled water and the concentration of acridine-modified ODN 32a was determined from the $A_{260}$ measurement. Theoretical yield for 29 nmole is 108 $\mu$g; actual yield was 39 $\mu$g. The purity of the ODN product 32a was determined by HPLC and PAGE.

Because some loss of ODN 32a occurred during the ultrafiltration step, an alternative method was used to purify the acridine-modified ODN 32a. Since all of the starting 3'-hexylamine-tailed ODN 32 reacted, purification of the acridine-modified ODN 32a was accomplished by gel filtration through a prepacked column containing Sephadex® G-25 (NAP-25 column, Pharmacia, Piscataway, N.J.). After equilibrating the column with 25 mL of water, the crude reaction mixture was applied and the acridine-modified ODN was eluted with water (0.5 mL fractions). The fractions containing pure product (as evidenced by C-18 HPLC) were combined and concentrated on a Speed-Vac. The pale yellow solid residue 32a was reconstituted with 200 $\mu$L of water and analyzed by UV at 260 nm. The concentration was determined to be 108 $\mu$g/200 $\mu$L. Theoretical yield is 108 $\mu$g.

EXAMPLE XXXII

Synthesis of 3'-Acridine-Tailed ODNs (33a, 33b). Using Amine-On CPG

The HPLC-purified 3'-amine-tailed ODN 33 was treated with acridine TFP ester (19 or 20) in pH 8.3 borate buffer, using the same reaction conditions as described above in Example XXXI. After shaking for several hours, HPLC analysis showed that approximately 70% of the "3'-amine tailed ODN 33" remained unreacted. PAGE analysis of the crude reaction mixture indicated that only the least mobile band reacted completely. Treatment with additional aliquots of borate buffer and 19 did not increase the extent of reaction. After 22 hours, the mixture was concentrated and small molecular weight impurities were removed by centrifugation through a 3,000 MW cutoff ultrafiltration membrane. The retentate was purified by C-18 HPLC and concentrated to give ODN 33a or 33b as a single peak by C-18 HPLC and one band by PAGE.

Table I shows properties of the modified and unmodified oligonucleotide 5'-TCCATGTTCGT.

TABLE I

| ODN[a] modifications | MW | $A_{260} = 1$[b] (μg/mL) | % yield[c] | HPLC, min[f] | PAGE, $Rm$[h] | $T_m$[j] °C. |
|---|---|---|---|---|---|---|
| target none | 6199 | 29.6 | 21 | 8.7 | 0.60 | — |
| control none | 3298 | 33.6 | 53 | 8.0 | 0.79 | 45.4–45.9 |
| 33 3'-amine (amine-ON) | 3451 | 35.2 | 42 | 9.0 | 0.80[i] | 45.9 |
| 34 3'-amine (hexylamine) | 3477 | 35.4 | 27 | 9.2 | 0.75 | 46.3 |
| 24 3'-CHOL | 3890 | 39.7 | 48 | 19.0[g] | 0.74 | 52.4 |
| 25 3'-ACR(3C) | 3710 | 36.4 | 43 | 11.1 | 0.75 | 52.7 |
| 26 3'-ACR(5C) | 3738 | 36.7 | 64 | 12.8 | 0.74 | 52.7 |
| 33a 3'-ACR(3C) | 3684 | 36.2 | 14 | 11.9 | 0.75 | 51.3 |
| 33b 3'-ACR(5C) | 3712 | 36.4 | 27 | 13.0 | 0.74 | 52.8 |
| 32a 3'-ACR(3C) | 3710 | 36.4 | 36[d],100[e] | 13.3 | — | 50.8 |

[a]Sequence of 20-mer ODN (target) is 5'-GTGACGAACATGGAGAACAT. Sequence of 11-mer ODN (control) is 5'-TCCATGTTCGT.
[b]Calculated concentration of ODN that gives 1.00 absorbance units at 260 nm.
[c]% Yield of isolated ODN from 1 μmole of CPG. Yield of 32a, 33a and 33b are based on μmoles of starting amine tailed ODN.
[d]Purified by C-18 HPLC.
[e]Purified by gel filtration.
[f]Elution time; HPLC system described in FIG. 1.
[g]A gradient of 35–80% acetonitrile (30 min) was used.
[h]Rm is the ratio of distance of migration relative to bromophenol blue.
[i]$R_m$ is given for the major component.
[j]$T_m$ is the temperature at the midpoint of the maximum slope of $A_{260}$ vs. temperature.

Scheme VIII shows the structure of the 3'-acridine tails that are incorporated into ODNs 25, 26, 32a, 33a, 33b. AH-CPG provided improved yields of 3'-acridine-tailed ODN, as compared to yields obtained with amine-ON CPG.

EXAMPLE XXXIII

Synthesis of Internal Amine-Modified ODNs (34–36)

Internal amine modifications were introduced using the protocol described in Example XXX in conjunction with the 5'-DMTr-3,-O-cyanoethyldiisopropyl-phosphoramidite derivative of 5-phthalimidopropyl-2'-deoxyuridine, as described by K. J. Gibson and S. J. Benkovic, *Nucl. Acids Res.* 15:6455 (1987). Briefly, the ODN 5'-TCCATGTTCGT was internally modified at positions a, b and/or c, as illustrated below:

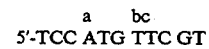

Three different ODNs were prepared with amine modifications at position a 34, positions a+b 35 or positions a+c 36.

EXAMPLE XXXIV

Synthesis of Internally Modified Acridine ODNs (34a, 34b, 35a, 35b, 36a, 36b)

Internally amine-modified ODNs 34, 35, and 36 were reacted with acridine TFP ester 19 according to the procedure described in Example XXXI (yielding ODN products 34a, 35a and 36a, respectively), or with acridine TFP ester 20 (yielding ODN products 34b, 35b and 36b, respectively).

EXAMPLE XXXV

Thermal Denaturation Studies

To examine the effects of the 3'-tail on binding affinity, $T_m$ studies were performed using various 3'-modified ODNs described above. Thermal dissociation curves were obtained by following changes in $A_{260}$ of aqueous solutions containing equimolar amounts of a selected 3'-tailed ODN and an appropriate complementary, unmodified 20-mer target ODN (5'-GTGAC-GAACATGGAGAACAT). The 20-mer ODN target provides nucleotide overhangs that may influence interactions with the 3'-modification of the ODN; such interactions likely will be important in the actual biological target. For these experiments, the target was DNA and not the likely biological target, RNA. The $T_m$ of an acridine-modified ODN-target duplex will increase if the acridine efficiently intercalates between the base pairs of the mini duplex upon hybridization with the target strand. An unmodified 11-mer ODN was used as a control in each $T_m$ study.

ODNs were prepared as 2 μM solutions in pH 7.2 PBS. A Gilford System 2600 UV-VIS spectrophotometer equipped with a Gilford 2527 Thermo-programmer was used. The samples were heated from 15° C. to 85° C. with a temperature increase of 0.5° C./min using a temperature controlled cuvette. Absorbance vs. time and the first derivative data were recorded automatically. The T, was determined using the derivative maxima. Duplicate experiments produced $T_m$s within 0.5° C. Data from one representative experiment are given in Table I (in Example XXXII).

A significant increase in the melting temperature of the 3'-cholesterol-tailed ODN 24 as compared to the unmodified ODN was observed, in contrast to similar studies of 3'-cholesterol-modified ODNs previously reported (R. L. Letsinger et al., Proc. Natl. Acad. Sci. USA 86:6553 (1989)). In the $T_m$ studies described herein, overhang of the complementary target, as well as interaction of lipophilic tails with the target nucleic acid, may influence $T_m$.

ODNs 25 and 26 showed comparable binding affinity for the target ODN (i.e., comparable $T_m$s). While no dramatic difference was observed between the $T_m$s of ODNs 25 and 26 (i.e., 3- and 5-carbon linker arm lengths), ODNs 33a and 32a resulted in slightly smaller increases in $T_m$, as compared to $\Delta T_m$s for ODNs 25, 26 and 33b. These data suggest that linker arm length, rigidity of the linker arm, stereochemical fidelity and/or sequence-dependent intercalation effects may influence $T_m$.

Table II presents $T_m$ data obtained with unmodified and internally modified ODNs (both single and double internal modifications).

TABLE II

Data for Internally Modified Acridine-ODNs

| ODN (modification) | position of U | $T_m$(°C.) | $\alpha T_m$(°C.) |
|---|---|---|---|
| control (none) | none | 45.5 | — |
| 34 (one amine) | a | 47.5 | +2.0 |
| 35 (two amines) | a, b | 47.2 | +1.7 |
| 36 (two amines) | a, c | 44.6 | −0.9 |
| 34a (3C acr) | a | 46.6 | +1.1 |
| 35a (3C acr) | a, b | 45.1 | −0.4 |
| 36a (3C acr) | a, c | 43.4 | −2.1 |
| 34b (5C acr) | a | 51.4 | +5.9 |
| 35b (5C acr) | a, b | 56.2 | +10.7 |
| 36b (5C acr) | a, c | 56.0 | +10.5 |

Target sequence: 3'-
position of U
Antisense 11-mer:
TAC AAG AGG TAC AAG CAG TG -5'
          a  bc
5=- TCC AUGUUC GT  -3'
U = 5-aminopropyl-2'-deoxyuridine The $T_m$ of unmodified and internally modified ODNs was determined, and the difference between unmodified ODN $T_m$ and the $T_m$ for each internally modified ODN was calculated ($\Delta T_m$ (° C.)). The calculated $T_m$ differences ranged from −2.1° to +10.7° C. While 5-carbon linker arm lengths resulted in larger $T_m$ increases (i.e., 34b, 35b, 36b), such large $T_m$ increases are not readily predictable. The inclusion of a second intercalating acridine group resulted in an additive effect on $T_m$ increase. These data suggest that linker arm length, sequence-dependent intercalation effects and/or hydrogen bonding of the amide linkages (generated through reaction of the amine modification with the acridine TFP ester) may influence $T_m$.

EXAMPLE XXXVI

O-(4,4'-dimethoxytrityl)-1,6-hexanediol (37)

To a solution of 3.38 g (10 mmol) of DMTr-Cl and 3.45 mL (20 mmol) of diisopropylethylamine in 50 mL of dry pyridine was added 5.91 g (50 mmol) of 1,6-hexanediol. After stirring for 4 h, the mixture was quenched with 85 mL of 5% sodium bicarbonate and extracted with 2×100 mL of methylene chloride. The organic phase was washed with 2×100 mL of water and 100 mL of brine, dried over sodium sulfate, filtered, and concentrated. The residue was purified by flash chromatography (3.5×17 cm silica) using methylene chloride. The fractions containing pure product were combined and concentrated to give 1.40 g of 37 as a yellow syrup.

TLC (95:5 methylene chloride:methanol), $R_f$=0.40, yellow spot which stained orange upon spraying with 10% sulfuric acid in methanol;

$^1$H NMR (CDCl$_3$) 7.5-7.1 (m, 9H), 6.81 (m, 4H), 3.80 (s, 3H), 3.77 (s, 3H), 3.64 (q, 2H, J=6.6 Hz), 3.02 (q, 2H, J=6.0 HZ), 1.7-1.2 (m, 8H).

Anal. Calc for C$_{27}$H$_{32}$O$_4$·0.7 H$_2$O: C, 74.87; H, 7.77. Found: C, 74.61; H, 7.36.

EXAMPLE XXXVII

Hexanol-CPG (3S)

To a stirred solution of 530 mg (1.26 mmol) of the alcohol 37 in 10 mL of dry pyridine was added 380 mg (3.80 mmol) of succinic anhydride and 76 mg of DMAP. The mixture was stirred under argon for 23 h and evaporated to dryness. Residual pyridine was removed by co-evaporation with toluene. The residue was dissolved in 30 mL of chloroform, washed with brine, dried over sodium sulfate and concentrated to give quantitative yield of the succinate as a yellow solid foam.

TLC (95:5/methylene chloride:methanol), $R_f$=0.19. Product appeared as a yellow spot which stained orange upon spraying with 10% sulfuric acid in methanol.

To 104 mg (0.200 mmol) of the crude succinylated derivative was added 1.0 g of acid-washed LCAA-CPG, 10 mL of dry pyridine, 0,080 mL of triethylamine, 380 mg (2.0 mmol) of EDC, and 12 mg of DMAP. The mixture was stirred under argon for 46 h. The CPG was filtered and washed with pyridine, methanol, chloroform and ether, then dried under vacuum. Residual amine groups on the CPG were capped by stirring the support in 3.5 mL of dry pyridine and 0.46 mL of acetic anhydride. After 3 h, the CPG was filtered, washed with methanol, chloroform and ether, then dried under vacuum to give 1.0 g of the product 38. The CPG was analyzed for DMTr content and found to have a loading of 26.2 μmol/g.

EXAMPLE XXXVIII

Synthesis of 3'-Hexanol-Tailed Calmodulin Antisense ODN (39)

Hexanol-CPG 38 corresponding to 1 μmole of DMTr content (38 mg) was packed into an empty ODN synthesis column (American Bionetics, Inc.). A 24-mer ODN with a sequence complementary to the initiation codon region (−12 to +12) of calmodulin mRNA of Paramecium (5'-TAATTATTCAGCCATTTAT-TAGTT) was prepared using hexanol-CPG 38, an ABI 380B DNA synthesizer using standard phosphoramidite chemistry, and the protocol supplied by the manufacturer. The 5'-DMTr protecting group was not removed. The ODN was cleaved from the solid support and deprotected by treatment with 2 mL of 30% ammonium hydroxide at 40°–44° C. for 24 h. The supernatant was injected directly on a PRP-1 reverse phase HPLC column (305×7.0 mm) using a linear gradient of 20%–45% acetonitrile in 0.1M TEAA (pH 7.5) over 25 min (flow rate=2 mL/min). The product was collected in one fraction and concentrated on a Speed-Vac to give the 5'-DMTr protected product. The DMTr group was removed by treatment with 300 μL of 80% acetic acid (80 min at 28° C.), and the 3'-hexanol-tailed ODN was precipitated with 100 μL of 2.4M sodium chloride and 4 mL of 1-butanol. The mixture was centrifuged, washed with i mL of ethanol, centrifuged, evaporated to dryness. The white solid residue was reconstituted with 1 mL of sterile distilled water and filtered through a 0.2 μm filter. The concentration of ODN 39 was 3.75 mg/mL, as determined from UV absorbance at 260 nm. Theoretical yield for 1 μmole is 7.49 mg. The purified ODN 39 was analyzed by HPLC on a Dynamax C-18 column (0.75×25 cm) using a linear gradient of 5%–45% acetonitrile in TEAA over 20 minutes (flow rate=1 mL/min). One major peak eluted at 9.9 min (greater than 95% purity). ODN 39 purity was confirmed by denaturing PAGE analysis (one band).

EXAMPLE XXXIX

Biological Effect of Hexanol-Tailed ODN 39

Swimming behavior of the ciliated protozoan *Paramecium tetraurelia* has been used as a model biological system to study antisense effect of injected ODN 39. The swimming behavior of *Paramecium tetraurelia* is controlled by the action of a series of ion channels in the cell membrane (voltage dependent Ca2+ and K+ channels and the $Ca^{2+}$ dependent Na+ and K+ channels). These ion channels act in concert to generate an action potential that results in the reversal of ciliary beating. Such reversal results in the Paramecium swimming backwards. The regulatory protein calmodulin plays a central role in the control of membrane potential and swimming behavior in Paramecium.

Figure 2:
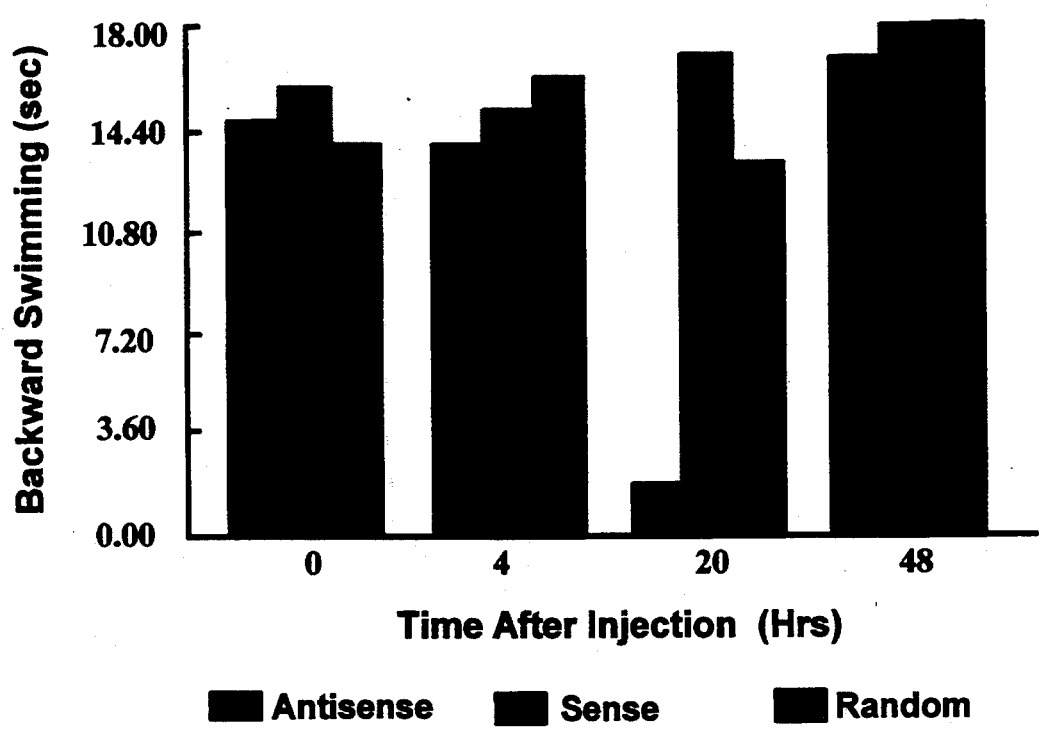
FIG. 2 presents a comparison of biological effect of antisense ODN 39 versus a random or "sense" ODN.

The 3'-hexanol-tailed antisense ODN 39 was used to inhibit the expression of the calmodulin gene in Paramecium. This antisense ODN 39 was microinjected into the cytoplasm of the cell and the behavior of the cell was monitored over time. The injected cells were assayed by incubation in a solution that tests the function of Na+ channels. Wild-type cells swim backwards for ≈15 sec in such solution; individual cells injected with the antisense ODN 39 displayed a significantly reduced behavioral response. After 15 to 20 h, backwards swimming time of the injected cells dropped to a minimum of ≈2 sec (FIG. 1). When cells microinjected with ODN 39 at time 0 were subsequently microinjected with calmodulin 15 h later, normal backwards swimming behavior was restored. Injection of a 24-mer 3'-hexanol-tailed ODN that represented either a random or "sense" sequence resulted in no change in backwards swimming (FIG. 2).

Figure 3:
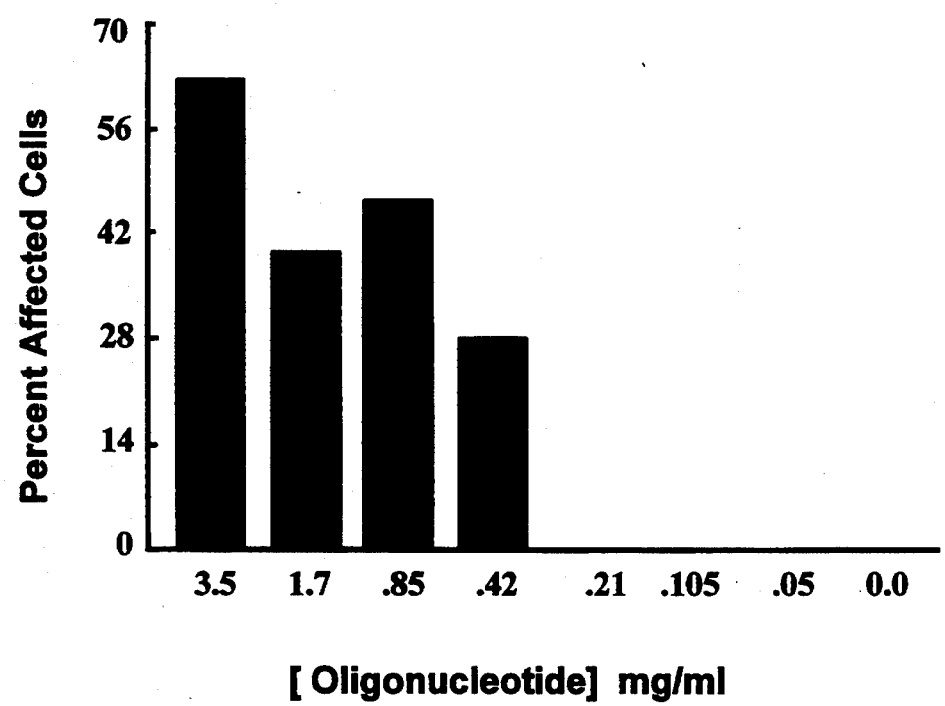
FIG. 3 is a dose response curve of antisense ODN 39 in the Paramecium swimming behavior assay.

The 3'-hexanol-tailed calmodulin antisense ODN 39 was effective at concentrations as low as 0.42 mg/mL (56 μM) (FIG. 3). In contrast, a calmodulin antisense ODN that had no 3'-modification showed no effect at concentrations as high as 6.1 mg/mL (835 μM). Thus, the 3'-tailed antisense ODN 39 demonstrated a potency at least 15-fold greater than that of the analogous unmodified ODN. This increase in potency may be attributable to improved stability of the 3'-tailed ODN to 3'-exonuclease degradation. Assuming an injection volume of 10 pL and a Paramecium volume of 200 pL, the minimum cytoplasmic concentration of ODN 39 for an observable biological effect was calculated to be 2.8 μM.

While, for illustrative purposes, this invention has been described with reference to its preferred embodiments, other embodiments, variations and/or modifications might be evident to the art skilled given this disclosure. As such, limitation of this invention is not to the preferred embodiments, but is as is set forth in the following claims.

SCHEME I

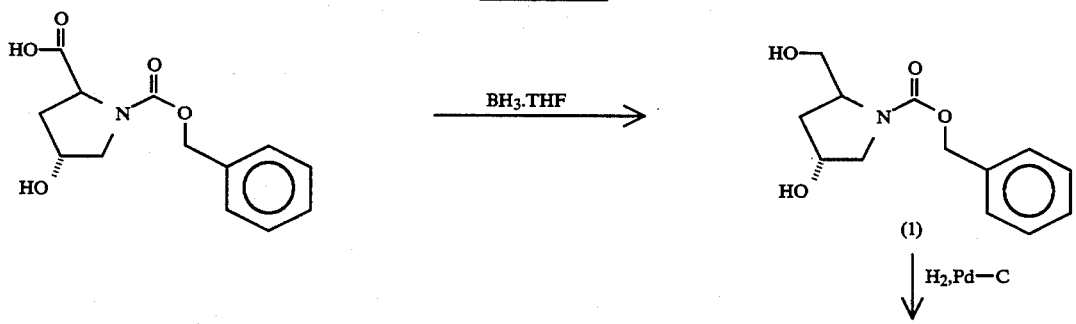

-continued
SCHEME I
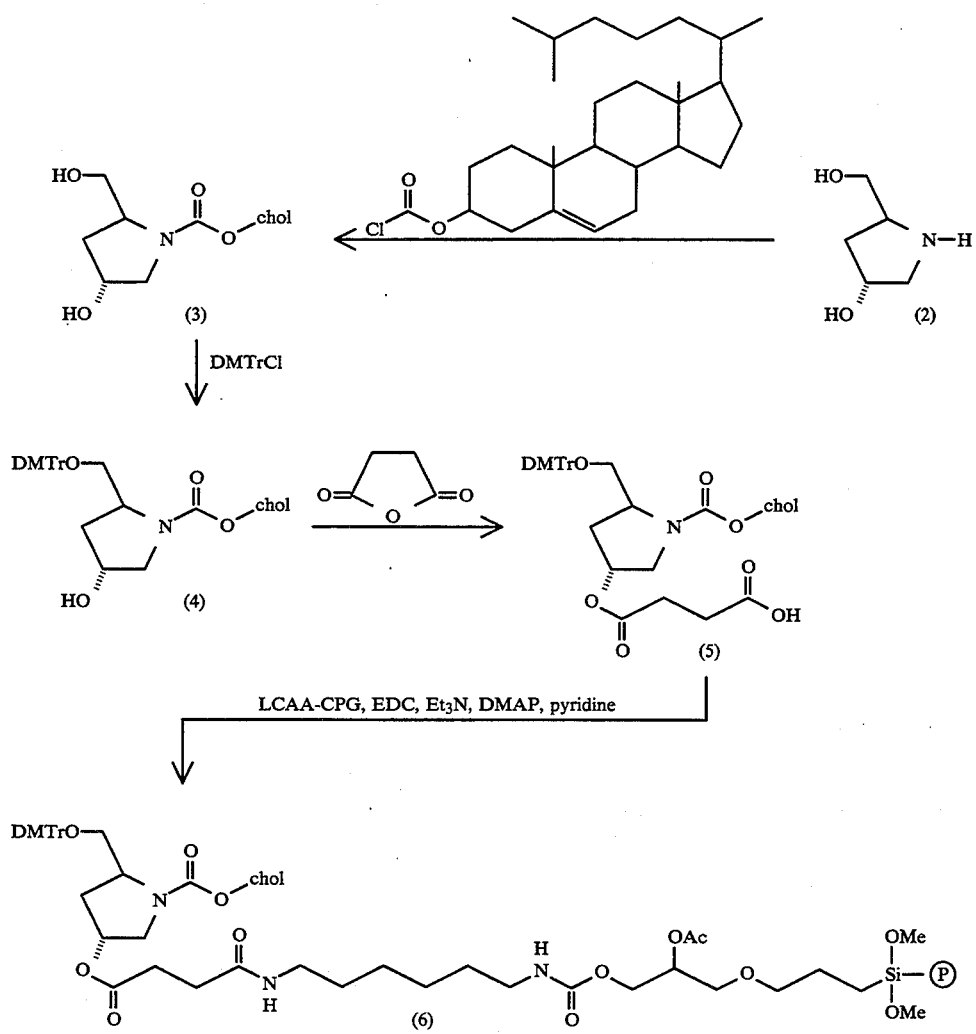
SCHEME II
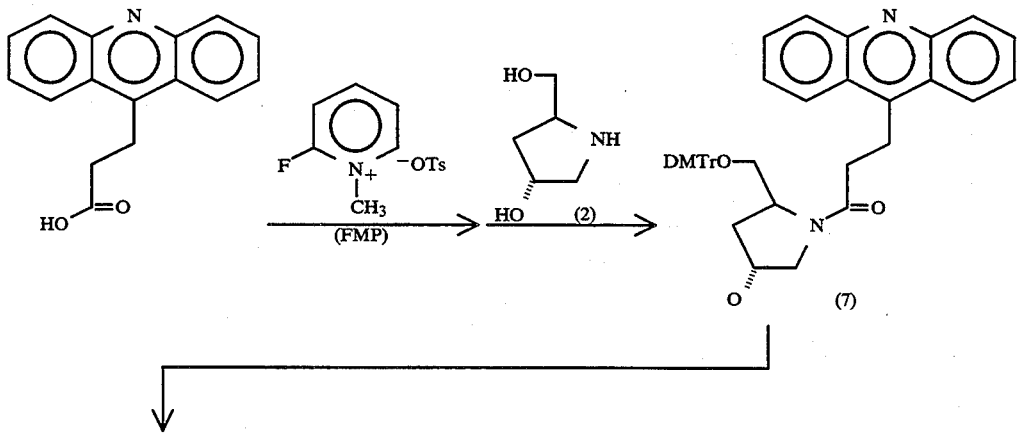

SCHEME II
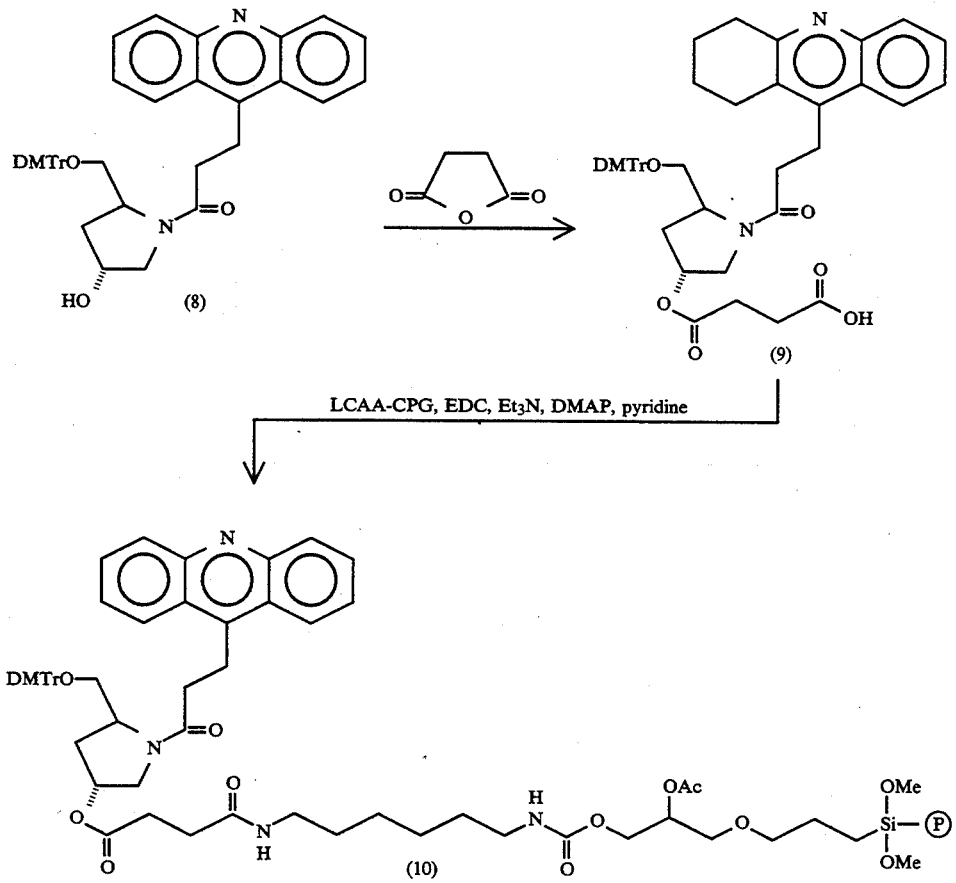
SCHEME III
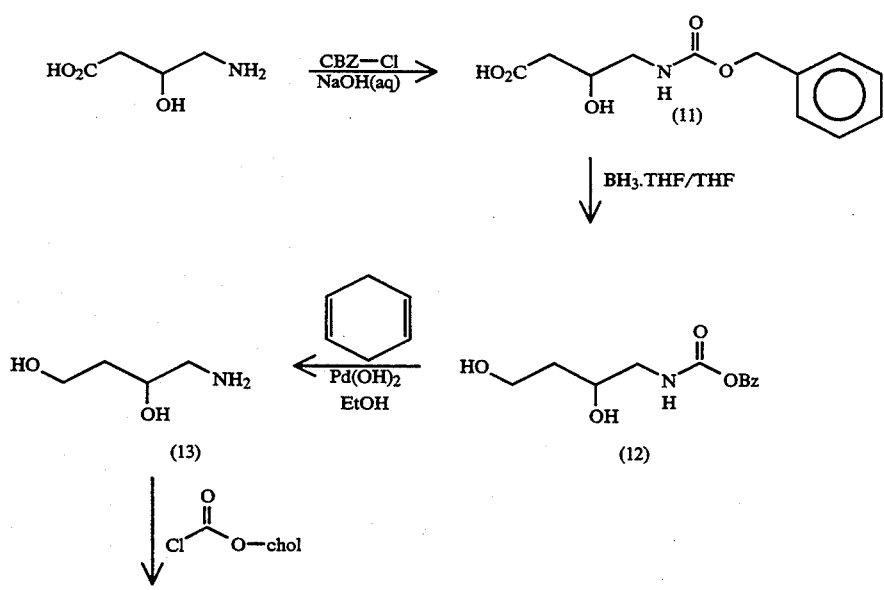

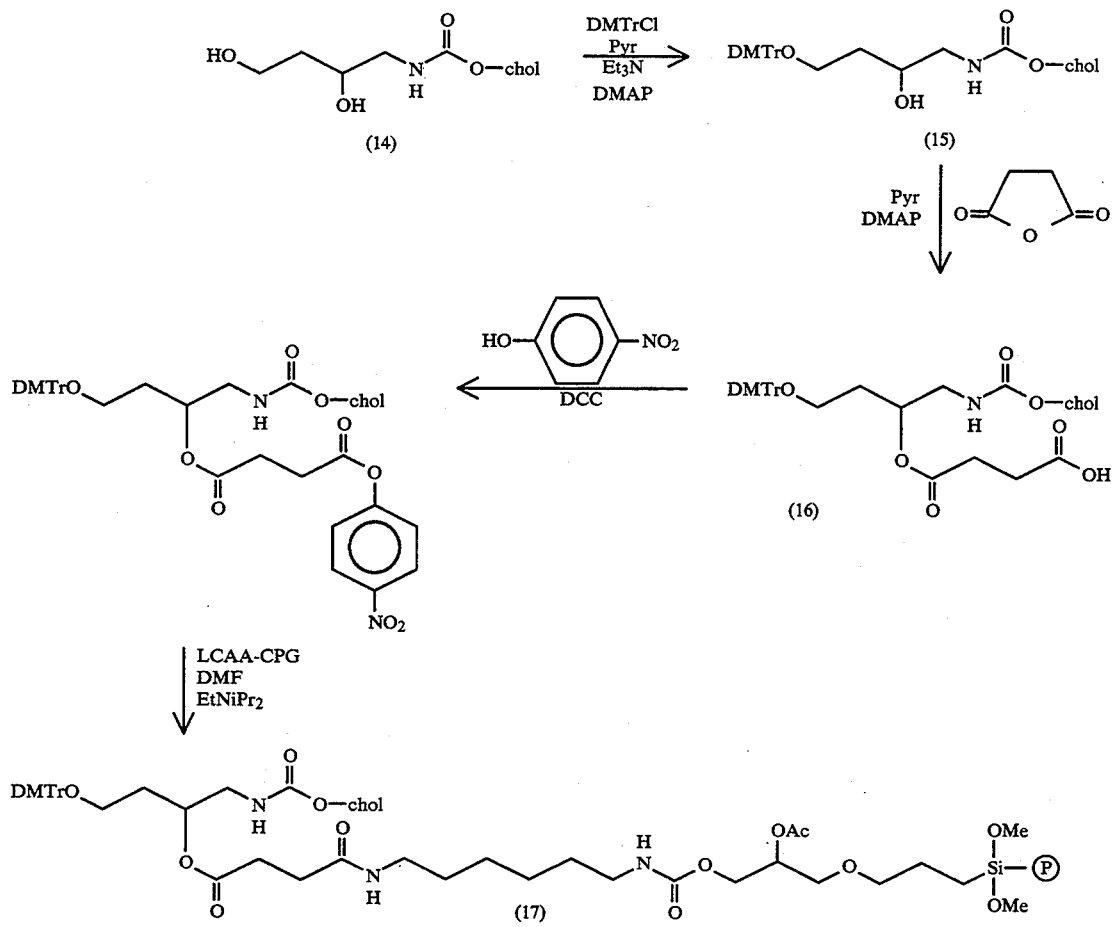
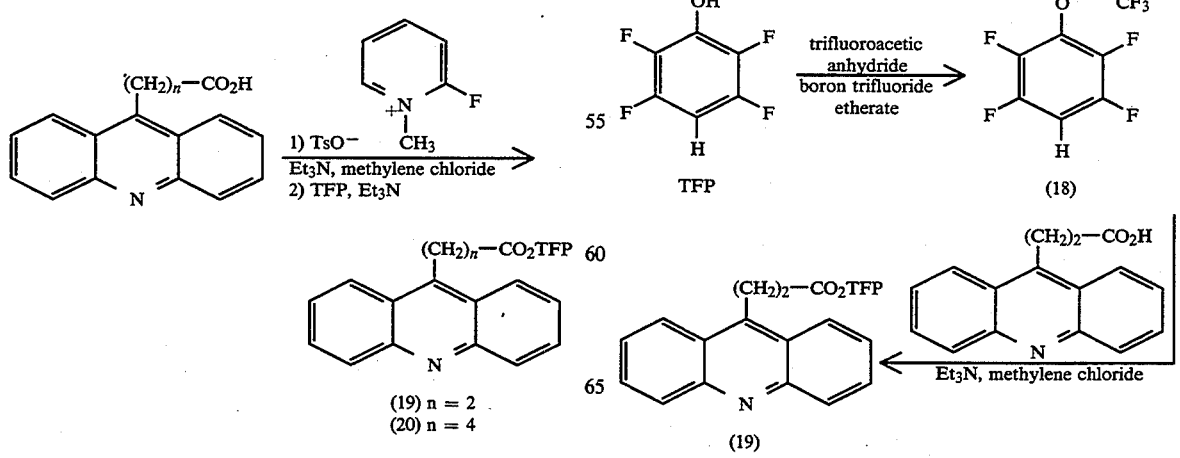

SCHEME V
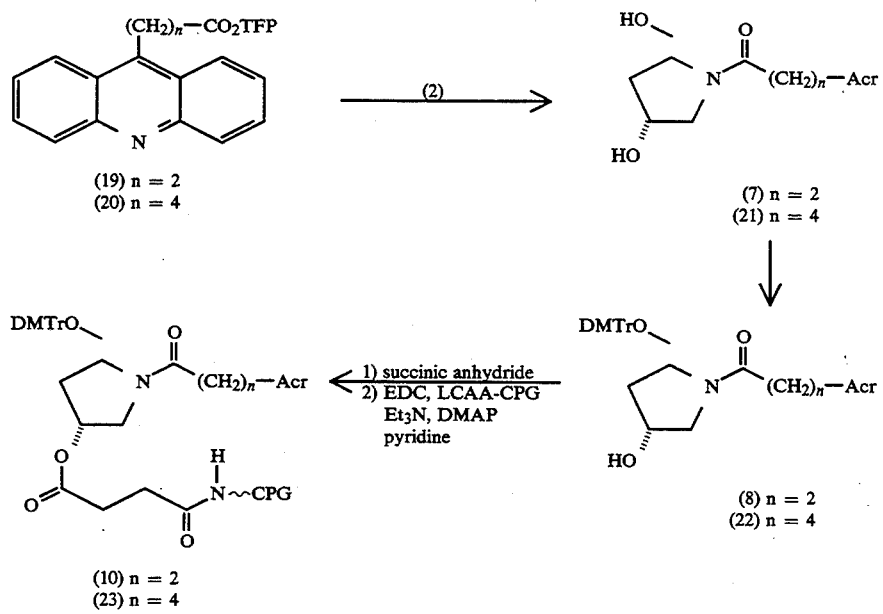
Scheme VI.
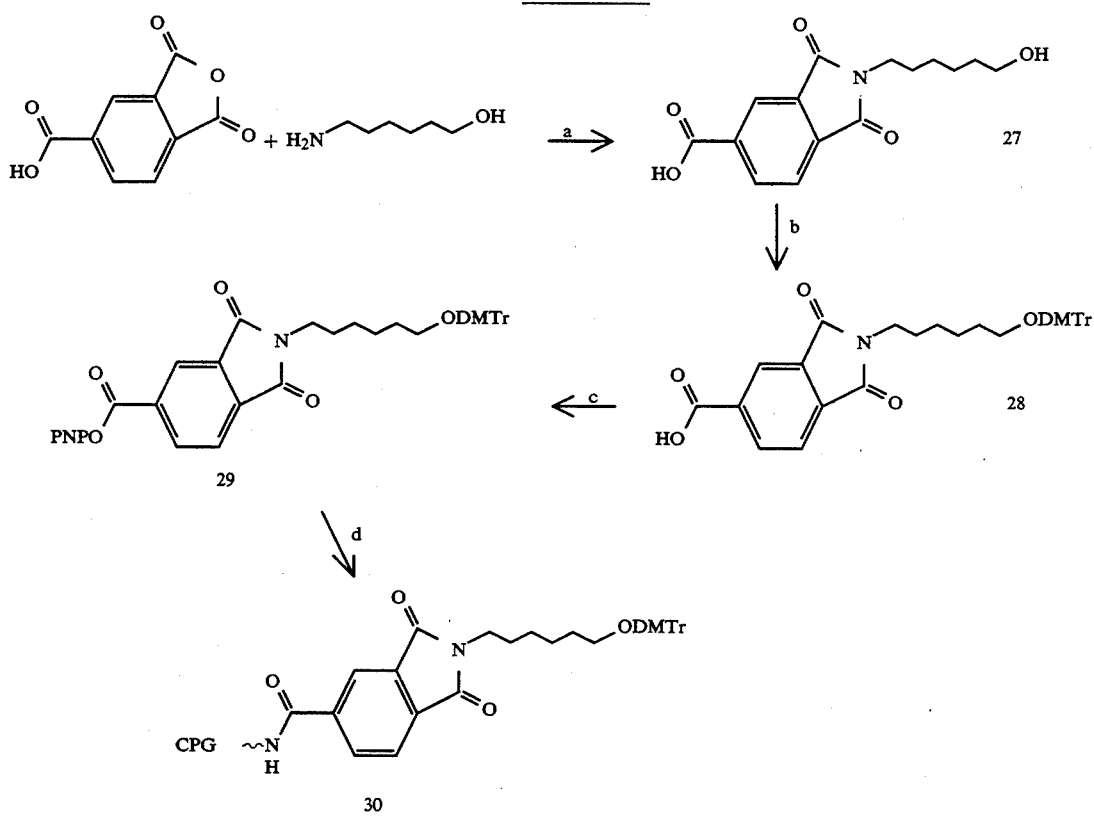
(a) fusion, 175–225 C;
(b) pyridine, Et$_3$N, DMTrCl;
(c) 1: p-nitrophenyl chloroformate, Et$_3$N, CH$_2$Cl$_2$; 2: DMAP;
(e) 1: pyridine, Et$_3$N; 2: Ac$_2$O.
Scheme VII: Synthesis of Hexanol-CPG

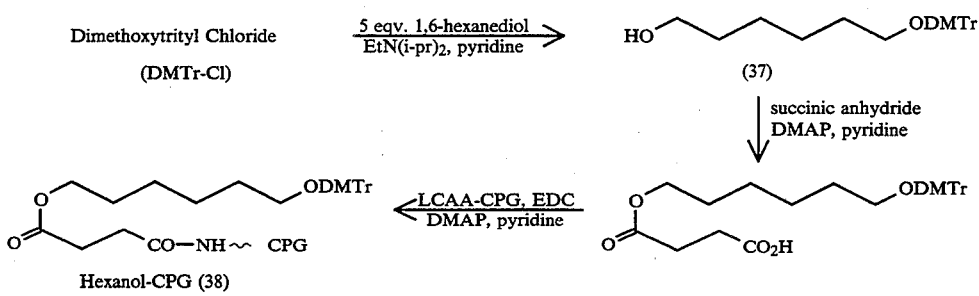

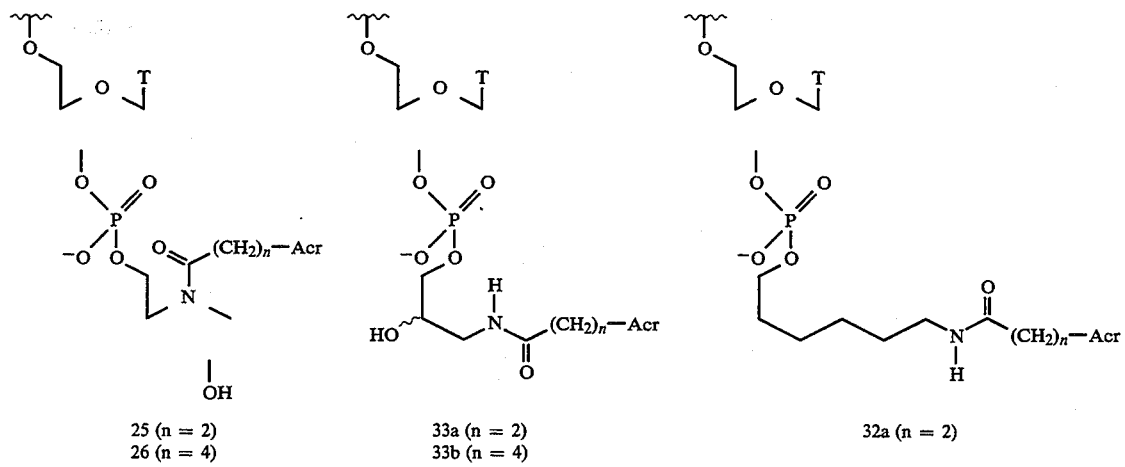

Scheme VIII: Structure of 3'-Modifications

We claim:

1. A solid support for oligonucleotide synthesis having the following structure:

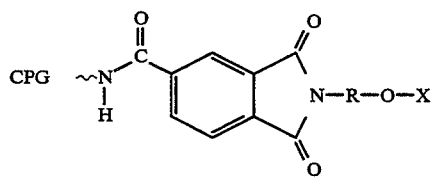

wherein CPG represents controlled pore glass,
the wavy line represents an alkylamine, which includes the amide nitrogen, covalently attached to the controlled pore glass,
X is H or 2,3'-dimethoxytrityl, and
R is alkyl, aryl, arylalkyl, heteroalkyl, or heteroaryl.

2. The solid support of claim 1 wherein R is $(CH_2)_n$ and n is an integer from 1–10.

3. The solid support of claim 1 wherein n is 6.

4. The solid support of claim 1 wherein X is H.

5. The solid support of claim 1 wherein X is 2,2'-dimethoxytrityl.

* * * * *

UNITED STATES PATENT AND TRADEMARK OFFICE
CERTIFICATE OF CORRECTION

PATENT NO. : 5,419,966
DATED : May 30, 1995
INVENTOR(S) : Reed et al.

It is certified that error appears in the above-indentified patent and that said Letters Patent is hereby corrected as shown below:

Column 8, line 52, "completing" should be --completed--;

Column 10, line 4, "indicated" should be --indicate--;

Column 11, line 15, after "for" please insert --the--;

Column 13, line 17, before "however" please insert --,--.

Signed and Sealed this

Ninth Day of April, 1996

BRUCE LEHMAN

Attest:

*Attesting Officer*  *Commissioner of Patents and Trademarks*

UNITED STATES PATENT AND TRADEMARK OFFICE
CERTIFICATE OF CORRECTION

PATENT NO. : 5,419,966

DATED : May 30, 1995

INVENTOR(S) : Reed et al.

It is certified that error appears in the above-identified patent and that said Letters Patent is hereby corrected as shown below:

Column 7, line 25, after "less" please insert --,--;

Column 8, line 61, "pyrolinol" should be --prolinol--;

Column 13, line 61, "i" should be --1--;

Column 16, line 23, "n" should be --L--;

Column 18, line 45, "his" should be --bis--;

Column 19, line 59, "Nucl. Acids Res. Res: 3113" should be --Nucl. Acids Res. 15: 3113--;

Column 20, line 9, "be " should be --10--;

Column 20, line 35, "$C_{13}H_{17}NO_4 \cdot 0.3H_2O$" should be --$C_{13}H_{17}NO_4 \cdot 0.3H_2O$--;

Column 21, line 19, "0,524" should be --0.524--;

Column 21, line 39, "2.78" should be --3.78--;

Column 21, line 40, "2.7-3.0" should be --3.7-3.0--;

Column 22, line 62, "15.mL" should be --1.5 mL--;

Column 22, line 64, "rosylate" should be --tosylate--;

Column 23, line 23, "2.SmL" should be --2.5 mL--;

Column 24, line 10, before "mg" please add --128--;

UNITED STATES PATENT AND TRADEMARK OFFICE
CERTIFICATE OF CORRECTION

PATENT NO. : 5,419,966
DATED : May 30, 1995
INVENTOR(S) : Reed et al.

It is certified that error appears in the above-identified patent and that said Letters Patent is hereby corrected as shown below:

Column 25, line 52, "121" should be --1:1--;
Column 25, line 53, "121" should be --1:1--
Column 25, line 54 "sluts " should be --elute--;

Column 25, line 57, "CDCl" should be --$CDCl_3$--;

Column 26, line 8, "421" should be --4:1--;

Column 27, line 13, "SmL" should be --8mL--;

Column 28, line 13, "2,3,5,6tetrafluorophenol" should be

--2,3,5,6-Tetraflourophenyl--;

Column 28, line 22, "$C_{8HO2}F_7$" should be --$C_8HO_2F_7$--;

Column 28, line 43 to column 29, line 11, please monve "$^1$H NMR ($CDCl_3$)...

Flourescence (pH 7.2) excitation at 355 nm, emission at 460 nm." to Column 29, before "EXAMPLE XXV";

Column 33, line 65, "3," should be --3'--;

Column 35, in Table II, the most right column, "$\triangleleft T_m(°C.)$" should be --$\Delta T_m(°C.)$--;

Column 35, in the notes of Table II, "5=" should be --5'--;

Column 36, line 39, "(3S)" should be --(38)--;

UNITED STATES PATENT AND TRADEMARK OFFICE
CERTIFICATE OF CORRECTION

PATENT NO. : 5,419,966

DATED : May 30, 1995

INVENTOR(S) : Reed et al.

It is certified that error appears in the above-identified patent and that said Letters Patent is hereby corrected as shown below:

Column 36, line 57, "0,080" should be --0.080--;

Column 37, line 28, "i mL" should be --1 mL--;

Column 38, line 1, "Ca2+" should be --$Ca^{2+}$--;

Column 42, formula (9), "

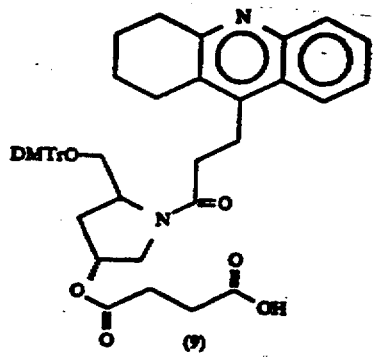

should be --

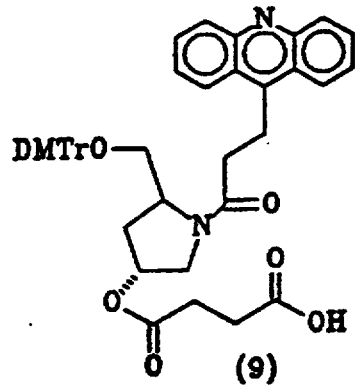

--;

UNITED STATES PATENT AND TRADEMARK OFFICE
CERTIFICATE OF CORRECTION

PATENT NO. : 5,419,966
DATED : May 30, 1995
INVENTOR(S) : Reed et al.

It is certified that error appears in the above-identified patent and that said Letters Patent is hereby corrected as shown below:

Col. 45, lines 4-26 <u>SCHEME V</u>

"

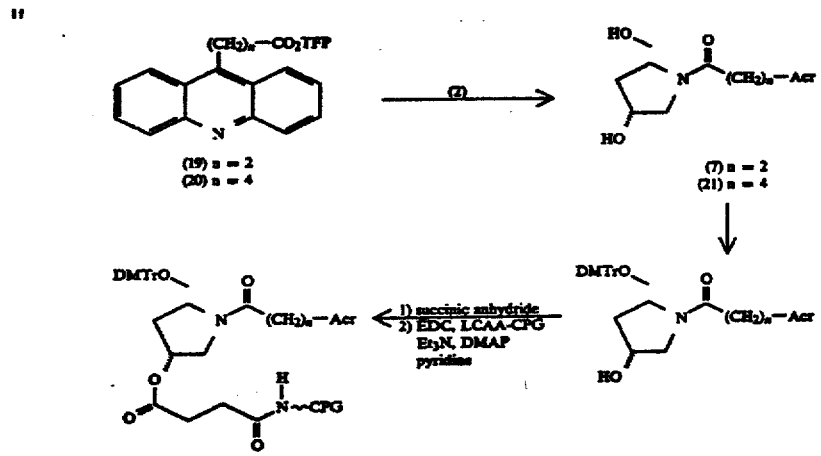

should be --

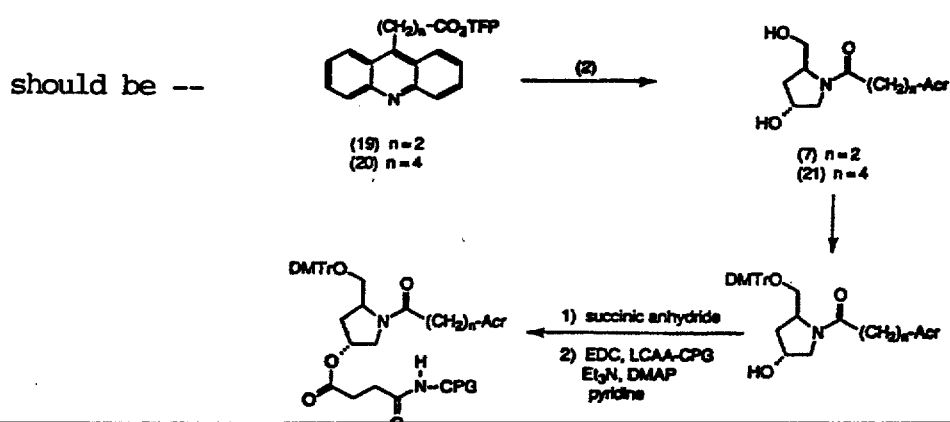

--

UNITED STATES PATENT AND TRADEMARK OFFICE
CERTIFICATE OF CORRECTION

PATENT NO. : 5,419,966
DATED : May 30, 1995
INVENTOR(S) : Reed et al.

It is certified that error appears in the above-indentified patent and that said Letters Patent is hereby corrected as shown below:

Column 47,48 SchemeVIII

"
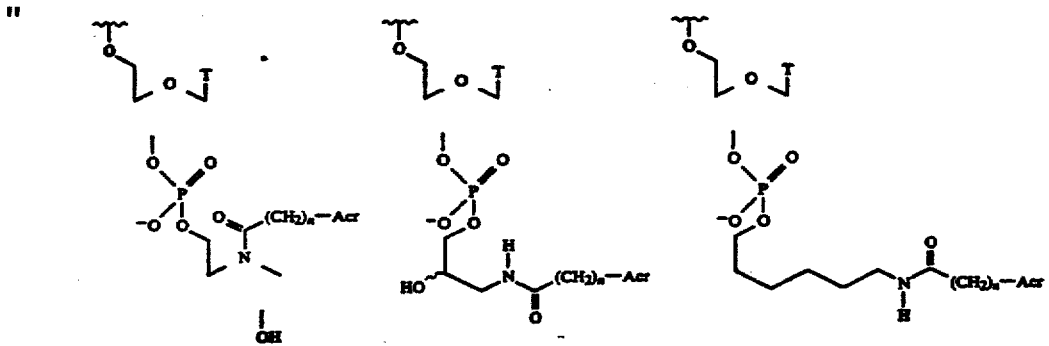

should be --

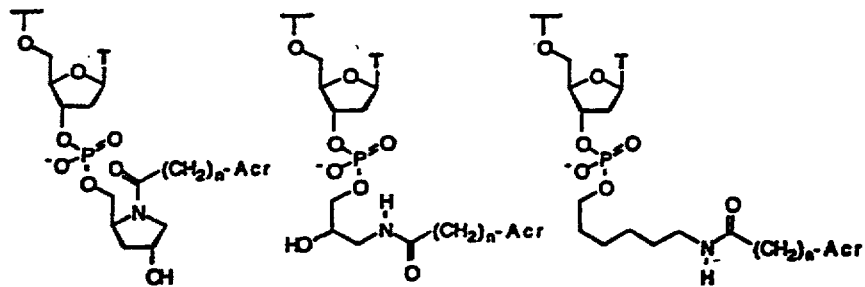

--.

UNITED STATES PATENT AND TRADEMARK OFFICE
CERTIFICATE OF CORRECTION

PATENT NO.  : 5,419,966
DATED       : May 30, 1995
INVENTOR(S) : Reed et al.

It is certified that error appears in the above-indentified patent and that said Letters Patent is hereby corrected as shown below:

Title page 1, left column, line 7 from the bottom, "Acid=Binding" should be
--Acid-Binding--;
Title page 1, left column, last line, "Support Art" should be
--Support Are--;
Title page 2, left column, line 2, "Slid Phase" should be --Solid-Phase--
Column 22, line 59, "9a-" should be --9-a- --.

Signed and Sealed this

Seventeenth Day of June, 1997

*Attest:*

BRUCE LEHMAN

*Attesting Officer*           *Commissioner of Patents and Trademarks*

UNITED STATES PATENT AND TRADEMARK OFFICE
CERTIFICATE OF CORRECTION

PATENT NO. : 5,419,966
DATED : May 30, 1995
INVENTOR(S) : Reed et al.

It is certified that error appears in the above-identified patent and that said Letters Patent is hereby corrected as shown below:

Column 1, line 5, before "BACKGROUND..." please insert the following paragraph --The U.S. Government has a nonexclusive, nontransferable, irrevocable paid-up license to practice or have practiced this invention for or on its behalf as provided for by the terms of Contract DAMD 17-88-C-8201 awarded by the U.S. Department of the Army.--.

Signed and Sealed this

Nineteenth Day of May, 1998

Attest:

BRUCE LEHMAN

*Attesting Officer*   *Commissioner of Patents and Trademarks*